United States Patent
Bühlmayer et al.

[11] Patent Number: 5,965,592
[45] Date of Patent: Oct. 12, 1999

[54] ACYL COMPOUNDS

[75] Inventors: Peter Bühlmayer, Arlesheim; Franz Ostermayer, Riehen; Tibur Schmidlin, Basel, all of Switzerland

[73] Assignee: Novartis Corporation, Summit, N.J.

[21] Appl. No.: 09/124,520

[22] Filed: Jul. 29, 1998

Related U.S. Application Data

[62] Division of application No. 08/294,925, Aug. 24, 1994, which is a continuation of application No. 07/998,755, Dec. 29, 1992, Pat. No. 5,399,578, which is a continuation of application No. 07/654,479, Feb. 13, 1991, abandoned.

[30] Foreign Application Priority Data

Feb. 19, 1990 [CH] Switzerland ............... 518/90
Jul. 5, 1990 [CH] Switzerland ............... 2234/90

[51] Int. Cl.$^6$ ............... A61K 31/41; A61K 31/235; C07C 229/38; C07D 257/04
[52] U.S. Cl. ............... 514/381; 514/539; 514/541; 514/544; 514/545; 514/785; 548/253; 560/37; 560/42; 562/444; 562/458

[56] References Cited

U.S. PATENT DOCUMENTS

| | | | |
|---|---|---|---|
| 3,426,022 | 2/1969 | Nakanishi et al. | 260/251.5 |
| 4,301,169 | 11/1981 | Yamanaka et al. | 424/273 |
| 4,333,943 | 6/1982 | Kurchacova et al. | 424/269 |
| 4,355,040 | 10/1982 | Furukawa et al. | 424/273 R |
| 4,551,279 | 11/1985 | Mueller et al. | 260/404 |
| 4,578,386 | 3/1986 | Lee | 514/241 |
| 4,714,702 | 12/1987 | Inouye et al. | 514/259 |
| 4,748,245 | 5/1988 | James | 544/316 |
| 4,755,518 | 7/1988 | Rafferty et al. | 514/269 |
| 4,816,463 | 3/1989 | Blankley et al. | 514/293 |
| 4,820,843 | 4/1989 | Aldrich et al. | 548/252 |
| 4,870,186 | 9/1989 | Aldrich et al. | 548/215 |
| 4,874,867 | 10/1989 | Aldrich et al. | 548/101 |
| 4,880,804 | 11/1989 | Carini et al. | 514/234 |
| 4,916,129 | 4/1990 | Carini | 514/235.2 |
| 4,921,632 | 5/1990 | Nakamura et al. | 252/299.1 |
| 5,015,651 | 5/1991 | Carini et al. | 514/381 |
| 5,037,829 | 8/1991 | Freyne et al. | 514/259 |
| 5,138,069 | 8/1992 | Carini et al. | 548/253 |
| 5,155,118 | 10/1992 | Carini et al. | 514/381 |
| 5,189,048 | 2/1993 | Carini et al. | 514/359 |
| 5,260,325 | 11/1993 | Markwalder et al. | 514/381 |
| 5,298,518 | 3/1994 | Miyake et al. | 514/381 |

FOREIGN PATENT DOCUMENTS

| | | |
|---|---|---|
| 2014008 | 10/1990 | Canada . |
| 324377 | of 0000 | European Pat. Off. . |
| 028834 | 5/1981 | European Pat. Off. . |
| 0142754 | 5/1985 | European Pat. Off. . |
| 148752 | 7/1985 | European Pat. Off. . |
| 245637 | 11/1987 | European Pat. Off. . |
| 253310 | 1/1988 | European Pat. Off. . |
| 291969 | 11/1988 | European Pat. Off. . |
| 323841 | 7/1989 | European Pat. Off. . |
| 392317 | 10/1990 | European Pat. Off. . |
| 399731 | 11/1990 | European Pat. Off. . |
| 399732 | 11/1990 | European Pat. Off. . |
| 400835 | 12/1990 | European Pat. Off. . |
| 400974 | 12/1990 | European Pat. Off. . |
| 401030 | 12/1990 | European Pat. Off. . |
| 403158 | 12/1990 | European Pat. Off. . |
| 403159 | 12/1990 | European Pat. Off. . |
| 407102 | 1/1991 | European Pat. Off. . |
| 409332 | 1/1991 | European Pat. Off. . |
| 411507 | 2/1991 | European Pat. Off. . |
| 412594 | 2/1991 | European Pat. Off. . |
| 412848 | 2/1991 | European Pat. Off. . |
| 419048 | 3/1991 | European Pat. Off. . |
| 420237 | 4/1991 | European Pat. Off. . |
| 425211 | 5/1991 | European Pat. Off. . |
| 425921 | 5/1991 | European Pat. Off. . |
| 426021 | 5/1991 | European Pat. Off. . |
| 427463 | 5/1991 | European Pat. Off. . |
| 429257 | 5/1991 | European Pat. Off. . |
| 430300 | 6/1991 | European Pat. Off. . |
| 430709 | 6/1991 | European Pat. Off. . |
| 432737 | 6/1991 | European Pat. Off. . |
| 434038 | 6/1991 | European Pat. Off. . |
| 434249 | 6/1991 | European Pat. Off. . |
| 19883/62 | 7/1961 | United Kingdom . |
| 89/06233 | 7/1989 | WIPO . |
| 91/00277 | 1/1991 | WIPO . |
| 91/00281 | 1/1991 | WIPO . |
| 91/07404 | 5/1991 | WIPO . |
| 91/14679 | 10/1991 | WIPO . |
| 91/15209 | 10/1991 | WIPO . |

*Primary Examiner*—Johann Richter
*Assistant Examiner*—Jane C. Oswecki
*Attorney, Agent, or Firm*—Marla J. Mathias

[57] ABSTRACT

Compounds of the formula

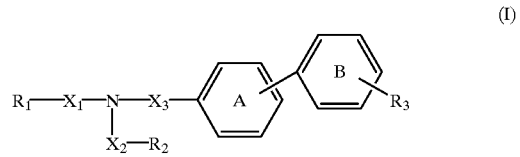

(I)

and their salts, in which $R_1$, is a $C_1$–$C_7$ aliphatic hydrocarbon radical; $X_1$ is —CO; $X_2$ is a divalent aliphatic hydrocarbon radical which comprises an ethyl group and an alkylene of 2 to 6 carbon atoms; $R_2$ is hydroxy, carboxy or alkoxycarbonyl in which alkoxy is from 1 to 7 carbon atoms; $X_3$ is a divalent aliphatic hydrocarbon; $R_3$ is carboxyl or 5-tetrazolyl; and the rings A and B independently of one another are otherwise unsubstituted; can be prepared in a known manner and may be used as active ingredients for medicaments.

6 Claims, No Drawings

ACYL COMPOUNDS

This is a division of application Ser. No. 08/294,925, filed Aug. 24, 1994, which is a continuation of application Ser. No. 07/998,755, filed Dec. 29, 1992, now U.S. Pat. No. 5,399,578, which is a continuation of application Ser. No. 07/654,479, filed Feb. 13, 1991, now abandoned.

The invention relates to compounds of the formula

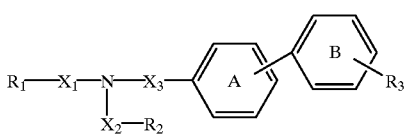

(I)

and their salts, in which
$R_1$ is an aliphatic hydrocarbon radical which is unsubstituted or substituted by halogen or hydroxyl, or a cycloaliphatic or aralphatic hydrocarbon radical; $X_1$ is CO or $SO_2$; $X_2$ is a divalent aliphatic hydrocarbon radical which is unsubstituted or substituted by hydroxyl or a cycloaliphatic or aromatic radical, or is a divalent cycloaliphatic hydrocarbon radical, it being possible for a carbon atom of the aliphatic hydrocarbon radical to be additionally bridged by a divalent aliphatic hydrocarbon radical; $R_2$ is carboxyl which, if desired, is esterified or amidated, substituted or unsubstituted amino, formyl which, if desired, is acetalised, hydroxyl which, if desired, is etherified, $S(O)_m$—R where m is 0, 1 or 2 and R is hydrogen or an aliphatic hydrocarbon radical, alkanoyl, unsubstituted or N-substituted sulfamoyl or $PO_nH_2$ where n is 2 or 3; $X_3$ is a divalent aliphatic hydrocarbon; $R_3$ is carboxyl, 5-tetrazolyl, $SO_3H$, $PO_2H_2$, $PO_3H_2$ or haloalkylsulfamoyl; and the rings A and B independently of one another are substituted or unsubstituted; processes for their preparation, pharmaceutical preparations and their use.

The compounds of the formula I can be present as salts, in particular pharmaceutically acceptable salts. If the compounds according to the invention have at least one basic centre, they can thus form acid addition salts. These are formed, for example, with inorganic acids, such as mineral acids, for example sulfuric acid, a phosphoric or hydrohalic acid, or with organic carboxylic acids, such as ($C_1$–$C_4$) alkanecarboxylic acids which are unsubstituted or substituted, for example by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, for example aspartic or glutamic acid, benzoic acid or with organic sulfonic acids, such as ($C_1$–$C_4$)alkane- or arylsulfonic acids which are unsubstituted or, for example by halogen, for example methane- or toluenesulfonic acid. Corresponding acid addition salts can also be formed with a basic centre which may additionally be present. In addition, the compounds according to the invention containing an acidic group (for example $R_3$=COOH or 5-tetrazolyl) can form salts with bases. Suitable salts with bases are, for example, metal salts, such as alkali metal or alkaline earth metal salts, for example sodium, potassium or magnesium salts, or salts with ammonia or of substituted organic amines, such as morpholine, thiomorpholine, piperidine, pyrrolidine, such as mono-, di- or tri-lower alkylmines (sic) or mono-, di- or tri-hydroxy lower alkylamines, for example mono-, di- or triethanolamine. Mono-lower alkylamines are, for example, ethyl- or tert-butylamine. Di-lower alkylamines are, for example, diethyl- or dipropylamine, and possible tri-lower alkylamines are, for example, triethyl- or tributylamine or dimethylpropylamine. Corresponding internal salts may furthermore be formed. Salts which are unsuitable for pharmaceutical uses are also included, as these are employed, for example, for the isolation or purification of compounds according to the invention or their pharmaceutically acceptable salts.

An aliphatic hydrocarbon radical is, for example, lower alkyl, lower alkenyl or secondarily lower alkynyl.

An aliphatic radical substituted by halogen or hydroxyl is, for example, halo-lower alkyl, -lower alkenyl or -lower alkynyl, or hydroxy-lower alkyl, -lower alkenyl or -lower alkynyl.

A cycloaliphatic hydrocarbon radical is in particular cycloalkyl and secondarily cycloalkenyl.

A suitable araliphatic radical is in particular phenyl-lower alkyl, also phenyl-lower alkenyl or -lower alkynyl.

A divalent hydrocarbon radical which bridges a C atom of an aliphatic radical $X_2$ is, for example, $C_2$–$C_6$alkylene, in particular $C_4$–$C_5$alkylene.

A cycloaliphatic radical is, for example, a cycloalkyl or, secondarily, cycloalkenyl which is unsubstituted, monosubstituted or, furthermore, polysubstituted, for example disubstituted, for example by carboxyl which, if desired, is esterified or amidated or formyl which, if desired, is acetalised.

An aromatic radical is, for example, a carbocyclic or heterocyclic aromatic radical, in particular phenyl or in particular an appropriate 5- or 6-membered and monocyclic radical which has up to four identical or different hetero atoms, such as nitrogen, oxygen or sulfur atoms, preferably one, two, three or four nitrogen atoms, an oxygen atom or a sulfur atom. Appropriate 5-membered heteroaryl radicals are, for example, monoaza-, diaza-, triaza-, tetraaza-, monooxa- or monothia-cyclic aryl radicals, such as pyrrolyl, pyrazolyl, imidazolyl, triazolyl, tetrazolyl, furyl and thienyl, while suitable appropriate 6-membered radicals are in particular pyridyl. Appropriate aromatic radicals are radicals which may be monosubstituted or polysubstituted, for example di- or trisubstituted, for example by identical or different radicals, for example selected from the group comprising: halogen, hydroxyl which, if desired, is etherified, $S(O)_m$—R and an aliphatic hydrocarbon radical which may be interrupted by —O— and which is unsubstituted or substituted by halogen or hydroxyl and which may be additionally substituted, for example by carboxyl which, if desired, is esterified or amidated or formyl which, if desired, is acetalised.

A divalent aliphatic hydrocarbon radical ($X_2$) is, for example, alkylene or alkylidene.

A divalent cycloaliphatic hydrocarbon radical is, for example, cycloalkylene.

Esterified carboxyl is, for example, carboxyl which is esterified by an alcohol which is derived from an aliphatic hydrocarbon radical, such as lower alkyl, phenyl-lower alkyl, lower alkenyl and secondarily lower alkynyl, and which may be interrupted by —O—, such as lower alkoxy-lower alkyl, -lower alkenyl and -lower alkynyl. Examples which may be mentioned are lower alkoxy-, phenyl-lower alkoxy-, lower alkenyloxy- and lower alkoxy-lower alkoxycarbonyl.

Amidated carboxyl is, for example, carbamoyl in which the amino group is unsubstituted or monosubstituted or, independently of one another, disubstituted by an aliphatic or araliphatic hydrocarbon radical or disubstituted by a divalent aliphatic hydrocarbon radical which may be interrupted by —O—, in particular lower alkylene or lower alkyleneoxy-lower alkylene. Examples of appropriately substituted amino groups which may be mentioned are lower alkyl-, lower alkenyl-, lower alkynyl-, phenyl-lower alkyl-, phenyl-lower alkenyl-, phenyl-lower alkynyl-, di-lower alkyl-, N-lower alkyl-N-phenyl-lower alkyl- and diphenyl-lower alkylamino and also lower alkylene- or lower alkyleneoxy-lower alkylene-amino.

Substituted amino has the meanings indicated in connection with substituted carbamoyl and is furthermore acylamino, such as lower alkanoyl-, phenyl-lower alkanoyl-, benzoyl-, lower alkanesulfonyl- or benzenesulfonylamino.

Acetalised formyl is, for example, di-lower alkoxymethyl or oxy-lower alkyleneoxymethylene.

Etherified hydroxyl is, for example, hydroxyl etherified by an alipahtic alcohol, in particular lower alkoxy or lower alkenyloxy, and is also a phenyl-lower alkoxy or phenoxy radical.

In N-substituted sulfamoyl, the substituted amino group has the meanings indicated in connection with substituted carbamoyl.

An aliphatic hydrocarbon radical which is interrupted by —O— is in particular lower alkoxy-lower alkyl, -lower alkenyl or -lower alkynyl, or lower alkenyloxy-lower alkyl, -lower alkenyl or -lower alkynyl.

Above and below, unsaturated aliphatic, cycloaliphatic and araliphatic substituents are primarily not linked to an aromatic radical via the C atom from which a multiple bond extends.

(Hetero)aromatic radicals, if not defined differently, are in particular in each case unsubstituted or mono- or polysubstituted, for example disubstituted or trisubstituted, in particular, for example, by a substitutent selected from the group comprising halogen, hydroxyl which, if desired, is etherified, $S(O)_m$—R and a hydrocarbon radical which is unsubstituted or substituted, for example by halogen or hydroxyl, and which may be interrupted by —O—.

The rings A and B are primarily a 4-biphenylyl, also a 2- or 3-biphenylyl ring system, where the radical $R_3$ is preferably located in the ortho-position of ring B. Correspondingly, the rings A and B are unsubstituted or monosubstituted or polysubstituted, for example disubstituted or trisubstituted, for example by identical or different radicals, for example selected from the group comprising: halogen, hydroxyl which, if desired, is etherified, $S(O)_m$—R and a hydrocarbon radical which is unsubstituted or substituted by halogen or hydroxyl and which may be interrupted by —O—.

The general definitions used above and below, unless defined differently, have the following meanings:

The expression "lower" means that corresponding groups and compounds in each case in particular comprise not more than 7, preferably not more than 4, carbon atoms.

Halogen is in particular halogen of atomic number not more than 35, such as fluorine, chlorine or bromine, and also includes iodine.

Alkanoyl is, for example, lower alkanoyl and is in particular $C_2$–$C_7$alkanoyl, such as acetyl, propionyl, butyryl, isobutyryl or pivaloyl. $C_2$–$C_5$alkanoyl is preferred.

Haloalkylsulfamoyl is in particular halo-$C_1$–$C_7$alkanesulfamoyl and is, for example, trifluoromethane-, difluoromethane-, 1,1,2-trifluoroethane- or heptafluoropropanesulfamoyl. Halo-$C_1$–$C_4$alkanesulfamoyl is preferred.

Lower alkyl is in particular $C_1$–$C_7$alkyl, for example methyl, ethyl, n-propyl, isopropyl, n-butyl, isobutyl, sec-butyl, tert-butyl, and also includes corresponding pentyl, hexyl and heptyl radicals. $C_1$–$C_4$alkyl is preferred.

Lower alkenyl is in particular $C_3$–$C_7$alkenyl and is, for example, 2-propenyl or 1-, 2- or 3-butenyl. $C_3$–$C_5$alkenyl is preferred.

Lower alkynyl is in particular $C_3$–$C_7$alkynyl and is preferably propargyl.

Halo-lower alkyl is in particular halo-$C_1$–$C_4$alkyl, such as trifluoromethyl, 1,1,2-trifluoro-2-chloroethyl or chloromethyl.

Halo-lower alkenyl is in particular halo-$C_3$–$C_5$alkenyl, such as 3-chloroallyl.

Halo-lower alkynyl is in particular halo-$C_3$–$C_5$alkynyl, such as 3-chloropropargyl.

Hydroxy-lower alkyl is in particular hydroxy-$C_1$–$C_4$alkyl, such as hydroxymethyl, 2-hydroxyethyl or 3-hydroxypropyl.

Hydroxy-lower alkenyl is in particular hydroxy-$C_3$–$C_5$alkenyl, such as 3-hydroxyallyl.

Hydroxy-lower alkynyl is in particular hydroxy-$C_3$–$C_5$alkynyl, such as 3-hydroxypropargyl.

Cycloalkyl is in particular $C_3$–$C_7$cycloalkyl and is, for example, cyclopropyl, cyclobutyl, cyclopentyl, cyclohexyl and cycloheptyl. Cyclopentyl and cyclohexyl are preferred.

Cycloalkenyl is in particular $C_3$–$C_7$cycloalkenyl and is preferably cyclopent-2- and -3-enyl, or cyclohex-2- and -3-en-yl.

Phenyl-lower alkyl is in particular phenyl-$C_1$–$C_4$alkyl and is preferably benzyl, 1- and 2-phenethyl, while phenyl-lower alkenyl and phenyl-lower alkynyl were (sic) in particular phenyl-$C_3$–$C_5$alkenyl and -alkynyl, in particular 3-phenylallyl and 3-phenylpropargyl.

Pyrrolyl is, for example, 2- or 3-pyrrolyl. Pyrazolyl is 3- or 4-pyrazolyl. Imidazolyl is 2- or 4-imidazolyl. Triazolyl is, for example, 1,3,5-1H-triazol-2-yl or 1,3,4-triazol-2-yl. Tetrazolyl is, for example, 1,2,3,4-tetrazol-5-yl, furyl is 2- or 3-furyl and thienyl is 2- or 3-thienyl, while suitable pyridyl is 2-, 3- or 4-pyridyl.

Alkylene is in particular $C_1$–$C_{10}$alkylene or lower alkylene, such as $C_1$–$C_7$alkylene, and is straight-chain or branched and is in particular methylene, ethylene, propylene and butylene and also 1,2-propylene, 2-methyl-1,3-propylene and 2,2-dimethyl-1,3-propylene. $C_1$–$C_5$alkylene is preferred.

Alkylidene is in particular $C_2$–$C_{10}$alkylidene, such as ethylidene, 1,1- or 2,2-propylidene, also 1,1- or 2,2-butylidene or 1,1-, 2,2- or 3,3-pentylidene. $C_2$–$C_5$alkylidene is preferred.

Cycloalkylene is in particular $C_3$–$C_7$cycloalkylene and is, for example, 1,2-cyclopropylene, 1,2- or 1,3-cyclobutylene, 1,2- or 1,3-cyclopentylene, 1,2-, 1,3- or 1,4-cyclohexylene and 1,2-, 1,3- or 1,4-cycloheptylene. 1,3-Cyclopentylene and 1,4-cyclohexylene are preferred.

Lower alkoxy is in particular $C_1$–$C_7$alkoxy and is, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. $C_1$–$C_4$alkoxy is preferred.

Lower alkoxy-lower alkyl is in particular $C_1$–$C_4$alkoxy-$C_1$–$C_4$alkyl, such as 2-methoxyethyl, 2-ethoxyethyl, 2-n-propyloxyethyl or ethoxymethyl.

Lower alkoxy-lower alkenyl or -lower alkynyl is in particular $C_1$–$C_5$alkoxy-$C_3$–$C_5$alkenyl or -$C_3$–$C_5$alkynyl.

Lower alkoxycarbonyl is in particular $C_2$–$C_8$alkoxycarbonyl and is, for example, methoxy-, ethoxy-, propyloxy- or pivaloyloxy-carbonyl. $C_2$–$C_5$alkoxycarbonyl is preferred.

Phenyl-lower alkoxycarbonyl is in particular phenyl-$C_1$–$C_4$alkoxycarbonyl and is, for example, benzyloxy-, 1- or 2-phenylethoxy-, 3-phenylpropyloxy- or 4-phenylbutyloxycarbonyl. Benzyloxycarbonyl is preferred.

Lower alkenyloxycarbonyl is in particular $C_3$–$C_5$alkenyloxycarbonyl, preferably allyloxycarbonyl, while lower alkynyloxycarbonyl is in particular $C_3$–$C_5$alkynyloxycarbonyl, such as propargyloxycarbonyl.

Lower alkoxy-lower alkoxycarbonyl is in particular $C_1$–$C_4$alkoxy-$C_1$–$C_4$alkoxycarbonyl, preferably ethoxyethoxycarbonyl, methoxyethoxycarbonyl and isopropyloxyethoxycarbonyl.

Lower alkyleneoxy-lower alkylene is in particular $C_1$–$C_4$alkyleneoxy-$C_2$–$C_4$alkylene, preferably ethyleneoxyethylene.

Lower alkylamino is in particular $C_1$–$C_7$alkylamino and is, for example, methyl-, ethyl-, n-propyl- and isopropyl-amino. $C_1$–$C_4$alkylamino is preferred.

Lower alkenylamino is preferably $C_3$–$C_5$alkylamino, such as allyl- and methallylamino.

Lower alkynylamino is preferably $C_3$–$C_5$alkynylamino, such as propargylamino.

Phenyl-lower alkylamino is preferably phenyl-$C_1$–$C_4$alkylarnino, in particular benzyl-, 1- and 2-phenylethylamino.

Phenyl-lower alkenylamino is preferably phenyl-$C_3$–$C_5$alkenylamino, in particular 3-phenylallylamino and 3-phenylmethallylamino.

Phenyl-lower alkynylamino is preferably phenyl-$C_3$–$C_5$alkynylamino, in particular 3-phenylpropargylamino.

Di-lower alkylamino is in particular di-$C_1$–$C_4$alkylamino, such as dimethyl-, diethyl-, di-n-propyl-, methylpropyl-, methylethyl-, methybutyl-amino and dibutylamino.

N-lower alkyl-N-phenyl-lower alkyl amino is in particular N-$C_1$–$C_4$alkyl-N-phenyl-$C_1$–$C_4$alkylamino, preferably methylbenzylamino and ethylbenzylamino.

Di-phenyl lower alkylamino is in particular di-phenyl-$C_1$–$C_4$alkylamino, preferably dibenzylamino.

Lower alkyleneamino is in particular $C_2$–$C_6$alkyleneamino, preferably pyrrolidin-1-yl or piperidin-1-yl.

Lower alkyleneoxy-lower alkyleneamino is in particular $C_2$–$C_3$-alkyleneoxy-$C_2$–$C_3$alkyleneamino, in particular morpholino.

Lower alkanoylamino is in particular $C_1$–$C_5$alkanoylamino, such as formyl-, acetyl-, propionyl-, butyryl- or pivaloylamino. $C_2$–$C_5$alkanoylamino is preferred.

Phenyl-lower alkanoylamino is in particular phenyl-$C_2$–$C_5$alkanoylamino, such as phenylacetyl- or phenylpropionylamino.

Lower-alkanesulfonylamino is in particular $C_1$–$C_7$alkanesulfonylamino, such as methane-, ethane-, propane- or butanesulfonylamino. $C_1$–$C_4$alkanesulfonylamino is preferred.

Lower alkenyloxy is in particular $C_3$–$C_7$alkenyloxy and is, for example, allyloxy or but-2-enyloxy or but-3-enyloxy. $C_3$–$C_5$alkenyloxy is preferred.

Phenyl-lower alkoxy is in particular phenyl-$C_1$–$C_4$alkoxy, such as benzyloxy, 1- or 2-phenylethoxy, 3-phenylpropyloxy or 4-phenylbutyloxy.

Lower alkenyloxy-lower alkyl is in particular $C_3$–$C_5$alkenyloxy-$C_1$–$C_4$alkyl, such as 2-allyloxyethyl, and lower alkenyloxy-lower alkenyl or -lower alkynyl is in particular $C_3$–$C_5$alkenyloxy-$C_3$–$C_5$alkenyl or -$C_3$–$C_5$alkynyl.

Extensive pharmacological investigations have shown that the compounds according to the invention have pronounced angiotensin II antagonist properties.

As is known, angiotensin II has strong vasoconstrictor properties, additionally stimulates aldosterone secretion and thus causes distinct sodium/water retention. The consequence of angiotensin II activity is manifested in an increase in blood pressure.

The importance of angiotensin II antagonists consists in suppressing the vasoconstrictor and aldosterone secretion-stimulating effects caused by angiotensin II by competitive inhibition of the binding of angiotensin II to the receptors.

The angiotensin II antagonist properties of the compounds according to the invention can be detected in the angiotensin II binding test. Rat smooth muscle cells from homogenized rat aorta are used here. The solid centrifugate is suspended in 50 mM tris buffer, pH 7.4, using peptidase inhibitors. Samples are incubated for 60 minutes at 25° C. with $^{125}$I-angiotensin II (0.175 nM) and a varying concentration of angiotensin II or the test substance. The incubation is then ended by addition of saline buffered with ice-cold phosphate, and the mixture is filtered through Whatman GF/F filters. The filters are counted using a gamma counter. The $IC_{50}$ values are determined from the dose-response curve. The concentrations which cause a 50% inhibition of the initial control values are given as $IC_{50}$ values. $IC_{50}$ values from about 1.0 nM were determined for the compounds according to the invention.

For the determination of angiotensin II-induced vasoconstriction, investigations on the isolated rabbit aorta ring can be used. For this purpose, rings are dissected from each chest aorta (sic) and fixed between 2 parallel clamps at an initial tension of 2 g. The rings are then immersed in 20 ml of a tissue bath at 37° C. and aerated with a mixture of 95% $O_2$ and 5% $CO_2$. The isometric reactions are measured. At 20-minute intervals, the rings are alternately stimulated with 10 nM angiotensin II (Hypertensin-CIBA) and 5 nM noradrenalin chloride. The rings are then incubated with selected concentrations of the test substances before treatment with the agonists. The data are analysed using a Buxo (sic) digital computer. $IC_{50}$ values from about 1 nM were determined for the compounds according to the invention.

The fact that the compounds according to the invention can reduce high blood pressure induced by angiotensin II can be verified in the normotensive anaesthetised rat test model. After calibration of the preparations with 0.9% NaCl (1 ml/kg i.v.), noradrenalin (1 μg/kg i.v.) or angiotensin II (0.3 μg/kg i.v.) in each case, increasing doses (3–6) of the test substance are intravenously injected by bolus injection, after which angiotensin II or noradrenalin is administered after each dose at 5 minute intervals. The blood pressure is measured directly in the carotid artery and recorded using an on-line data recording system (Buxco). The specificity of the angiotensin II antagonism is shown by the selective inhibition of the pressure effect produced by angiotensin II, but not that produced by noradrenalin. In these investigations, the compounds according to the invention showed an inhibiting effect from a dose of about 0.3 mg/kg i.v.

The antihypertensive activity of the compounds according to the invention may also be manifested in the renally hypertensive rat. High blood pressure is produced in male rats by constricting a renal artery according to the Goldblatt method. Doses of the substance are adm inist ered to t he rats by means of a stomach tube. Control animals receiv e an equivalent volume of solvent. Blood pressure and heart beat are measured indirectly at intervals in conscious animals by the tail clamp method of Gerold et al. [Helv. Physiol. Acta 24, 58, 1966] before administration of the substances or of the placebo and during the course of the experiments. It was possible to detect the pronounced antihypertensive effect below a dose of about 30 mg/kg p.o.

The compounds of the formula I can therefore be used, for example, as pharmaceutical active ingredients, such as antihypertensives, for example for the treatment of high blood pressure and cardiac insufficiency. The invention also relates to the use of the compounds according to the invention for the production of medicaments, in particular angiotensin II antagonists and antihypertensives, and to the use of these compounds for the therapeutic treatment of high blood pressure and cardiac insufficiency. The industrial production of the active substances is also included in the production of the pharmaceuticals.

The invention relates in particular to compounds of the formula I and their salts in which $R_1$ is an aliphatic hydrocarbon radical which is unsubstituted or substituted by halogen or hydroxyl, or a cycloaliphatic or araliphatic hydrocarbon radical; $X_1$ is CO or $SO_2$; $X_2$ is a divalent aliphatic hydrocarbon radical which is unsubstituted or substituted by hydroxyl or a cycloaliphatic or aromatic radical; $R_2$ is carboxyl which, if desired, is esterified or amidated, substituted or unsubstituted amino, forrnyl which, if desired, is acetalised, hydroxyl which, if desired, is etherified, $S(O)_m$—R where m is 0, 1 or 2 and R is hydrogen or an aliphatic hydrocarbon radical, alkanoyl, unsubstituted or N-substituted sulfamoyl or $PO_nH_2$ where n is 2 or 3; $X_3$ is —$CH_2$—; $R_3$ is carboxyl, 5-tetrazolyl, $SO_3H$, $PO_2H_2$, $PO_3H_2$ or haloalkylsulfamoyl; and the rings A and B independently of one another are substituted or unsubstituted.

The invention relates in particular to compounds of the formula I and their salts in which $R_1$ is lower alkyl, lower alkenyl, lower alkynyl, halo-lower alkyl, -lower alkenyl or -lower alkynyl, hydroxy-lower alkyl, -lower alkenyl or -lower alkynyl, cycloalkyl, cycloalkenyl, phenyl-lower alkyl, phenyl-lower alkenyl or phenyl-lower alkynyl; $X_1$ is CO or $SO_2$; $X_2$ is alkylene or alkylidene which is unsubstituted or substituted by hydroxyl, a cycloalkyl or cycloalkenyl radical, a phenyl radical or a 5- or 6-membered, monocyclic heteroaromatic radical having up to four identical or different hetero atoms, where the cyclic radicals, for their part, are unsubstituted or substituted by carboxyl which is free or esterified by an alcohol which is derived from lower alkyl, phenyl-lower alkyl, lower alkenyl, lower alkynyl or lower alkoxy-lower alkyl, -lower alkenyl or -lower alkynyl, carbamoyl in which the amino group is unsubstituted or monosubstituted or, independently of one another, disubstituted by lower alkyl, lower alkenyl, lower alkynyl, phenyl-lower alkyl, phenyl-lower alkenyl or phenyl-lower alkynyl or disubstituted by lower alkylene- or lower alkyleneoxy-lower alkylene, forrnyl, di-lower alkoxymethyl or oxy-lower alkyleneoxymethylene; $R_2$ is carboxyl which is free or esterified by an alcohol which is derived from lower alkyl, phenyl-lower alkyl, lower alkenyl, lower alkynyl or lower alkoxy-lower alkyl, -lower alkenyl or -lower alkynyl; carbamoyl in which the amino group is unsubstituted or monosubstituted or, independently of one another, disubstituted by lower alkyl, lower alkenyl, lower alkynyl, phenyl-lower alkyl, phenyl-lower alkenyl or phenyl-lower alkynyl or disubstituted by lower alkylene- or lower alkyleneoxy-lower alkylene; amino in which the amino group is unsubstituted or monosubstituted or, independently of one another, disubstituted by lower alkyl, lower alkenyl, lower alkynyl, phenyl-lower alkyl, phenyl-lower alkenyl or phenyl-lower alkynyl or disubstituted by lower alkylene- or lower alkyleneoxy-lower alkylene; lower alkanoyl-, phenyl-lower alkanoyl-, benzoyl-, lower alkanesulfonyl- or benzenesulfonyl-amino; formyl, di-lower alkoxymethyl, oxy-lower alkyleneoxymethylene, hydroxyl, lower alkoxy, lower alkenyloxy, phenyl-lower alkoxy, phenoxy, $S(O)_m$—R where m is 0, 1 or 2 and R is hydrogen, lower alkyl, lower alkenyl or lower alkynyl; lower alkanoyl, sulfamoyl in which the amino group is unsubstituted or monosubstituted or, independently of one another, disubstituted by lower alkyl, lower alkenyl, lower alkynyl, phenyl-lower alkyl, phenyl-lower alkenyl or phenyl-lower alkynyl or disubstituted by lower alkylene- or lower alkyleneoxy-lower alkylene, or is $PO_nH_2$ where n is 2 or 3; $X_3$ is —$CH_2$—; $R_3$ is carboxyl, 5-tetrazolyl, $SO_3H$, $PO_2H_2$, $PO_3H_2$ or halo-lower alkylsulfamoyl; where (hetero)aromatic radicals including the rings A and B are independently of one another in each case unsubstituted or substituted by one or more substituents selected from the group comprising halogen, hydroxyl, lower alkoxy, lower alkenyloxy, or lower alkyl, lower alkenyl, lower alkynyl, lower alkoxy-lower alkyl, -lower alkenyl, -lower alkynyl, lower alkenyloxy-lower alkyl, lower alkenyl and -lower alkynyl which are in each case unsubstituted or substituted by halogen or hydroxyl.

The invention relates in particular to compounds of the formula I and their salts, in which $X_2$ is alkylene or alkylidene which is unsubstituted or substituted by hydroxyl, a cycloalkyl or cycloalkenyl radical, a phenyl radical or a 5- or 6-membered, monocyclic heteroaromatic radical having up to four identical or different hetero atoms, it being possible for a C atom of alkylene or alkylidene to be bridged by $C_2$–$C_6$alkylene and the cyclic radicals, for their part, being unsubstituted or substituted by carboxyl which is free or esterified by an alcohol which is derived from lower alkyl, phenyl-lower alkyl, lower alkenyl, lower alkynyl, or lower alkoxy-lower alkyl, -lower alkenyl or -lower alkynyl, carbamoyl in which the amino group is unsubstituted or monosubstituted or, independently of one another, disubstituted by lower alkyl, lower alkenyl, lower alkynyl, phenyl-lower alkyl, phenyl-lower alkenyl or phenyl-lower alkynyl or disubstituted by lower alkylene- or lower alkyleneoxy-lower alkylene, formyl, di-lower alkoxymethyl or by oxy-lower alkyleneoxymethylene, or $X_2$ is $C_3$–$C_7$cycloalkylene; $X_3$ is lower alkylene or lower alkylidene; and the variables $X_1$, $R_1$, $R_2$ and $R_3$ have the meanings indicated immediately above and the (hetero)aromatic rings including the rings A and B can be substituted as indicated immediately above.

The invention relates in particular to compounds of the formula I and their salts, in which $R_1$ is lower alkyl, lower alkenyl, halo-lower alkyl or -lower alkenyl, hydroxy-lower alkyl, 3- to 7-membered cycloalkyl or phenyl-lower alkyl; $X_1$ is CO or $SO_2$; $X_2$ is $C_1$–$C_{10}$alkylene or $C_1$–$C_7$alkylidene which is unsubstituted or substituted by hydroxyl, a 3- to 7-membered cycloalkyl, 3- to 7-membered cycloalkenyl, phenyl, pyrroyl (sic), pyrazolyl, imidazolyl, triazolyl, tetrazolyl, furyl, thienyl or pyridyl radical which, for its part, can be unsubstituted or additionally substituted by carboxyl, lower alkoxycarbonyl, phenyl-lower alkoxycarbonyl, carbamoyl in which the amino group is unsubstituted or monosubstituted or, independently of one another, disubstituted by lower alkyl or phenyl-lower alkyl; formyl, di-lower alkoxymethyl or oxy-lower alkyleneoxymethylene; $R_2$ is carboxyl, lower alkoxy-, phenyl-lower alkoxy-, lower alkenyloxy- or lower alkoxy-lower alkoxy-carbonyl, carbamoyl in which the amino group is unsubstituted or monosubstituted or, independently of one another, disubstituted by lower alkyl or phenyl-lower alkyl or disubstituted by lower alkylene- or lower alkyleneoxy-lower alkylene; amino in which the amino group is unsubstituted or monosubstituted or, independently of one another, disubstituted by lower alkyl or phenyl-lower alkyl or disubstituted by lower alkylene- or lower alkyleneoxy-lower alkylene; lower alkanoyl, phenyl-lower alkanoyl-, benzoyl-, lower alkanesulfonyl- or benzenesulfonyl-amino, formyl, di-lower alkoxymethyl, oxy-lower alkyleneoxymethylene, oxyl, lower alkoxy, phenyl-lower alkoxy, phenoxy, $S(O)_m$—R where m is 0, 1 or 2 and R is lower alkyl; lower alkanoyl, sulfamoyl in which the amino group is unsubstituted or monosubstituted or, independently of one another, disubstituted by lower alkyl or phenyl-lower alkyl; or $PO_nH_2$ where n is 2 or 3; $X_3$ is methylene; $R_3$ is carboxyl, 5-tetrazolyl, $SO_3H$, $PO_2H_2$, $PO_3H_2$ or halo-lower alkylsulfamoyl; (hetero)aromatic radicals including the rings A and B are in each case unsubstituted or additionally substituted by one or more substituents selected from the group comprising halogen, hydroxyl, lower alkoxy, and lower alkyl or lower alkoxy-lower alkyl which is in each case unsubstituted or substituted by halogen or hydroxyl.

The invention relates in particular to compounds of the formula I and their salts in which $X_2$ is $C_1$–$C_{10}$alkylene or $C_1$–$C_7$alkylidene which is unsubstituted or optionally substituted by hydroxyl, a 3- to 7-membered cycloalkyl, 3- to 7-membered cycloalkenyl, phenyl, pyrrolyl, pyrazolyl, imidazolyl, triazolyl, tetrazolyl, furyl, thienyl or pyridyl radical which, for its part, can be unsubstituted or additionally substituted by carboxyl, lower alkoxycarbonyl, phenyl-lower alkoxycarbonyl, carbamoyl in which the amino group is unsubstituted or monosubstituted or, independently of one another, disubstituted by lower alkyl or phenyl-lower alkyl, formyl, di-lower alkoxymethyl or by oxy-lower alkyleneoxymethylene, where a C atom of alkylene or alkylidene can be bridged by $C_2$–$C_6$alkylene, or $X_2$ is $C_3$–$C_7$cycloalkylene; $X_3$ is lower alkylene or lower alkylidene and the variables $X_1$, $R_1$, $R_2$ and $R_3$ have the meanings indicated immediately above and the (hetero) aromatic rings including the rings A and B can be substituted as indicated immediately above.

The invention relates in particular to compounds of the formula I and it salts in which the variables $R_1$, $X_1$ and $R_3$ have the meanings in each case indicated above; $X_2$ is lower alkylene or lower alkylidene which is unsubstituted or substituted by hydroxyl, 3- to 7-membered cycloalkyl, phenyl or imidazolyl and $R_2$ is carboxyl, lower alkoxy-, phenyl-lower alkoxy- or lower alkoxy-lower alkoxy-carbonyl, carbamoyl which is unsubstituted or monosubstituted or, independently of one another, disubstituted by lower alkyl or phenyl-lower alkyl, amino, lower alkanoyl-, phenyl-lower alkanoyl- or lower alkanesulfonylamino, hydroxyl, lower alkoxy, phenyl-lower alkoxy or phenoxy; $X_3$ is —CH$_2$—; where (hetero)aromatic radicals including the rings A and B are in each case unsubstituted or substituted unsubstituted or substituted (sic) by one or more substituents selected from the group comprising halogen, trifluoromethyl, hydroxyl, lower alkoxy, lower alkyl, hydroxy-lower alkyl or lower alkoxy-lower alkyl.

The invention relates in particular to compounds of the formula I and their salts in which $X_2$ is lower alkylene or lower alkylidene which is unsubstituted or substituted by hydroxyl, 3- to 7-membered cycloalkyl, 7-membered cycloalkenyl, phenyl or imidazolyl, where a C atom of lower alkylene or lower alkylidene can be bridged by $C_2$–$C_6$alkylene, or $X_2$ is $C_3$–$C_7$cycloalkylene; and the variables $X_1$, $X_3$, $R_1$, $R_2$ and $R_3$ have the meanings indicated immediately above and the rings A and B can be substituted as indicated immediately above.

The invention relates in particular to compounds of the formula

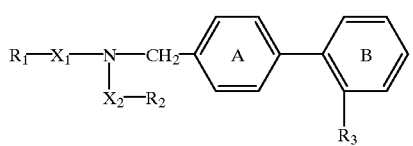

and their salts in which the variables $R_1$, $X_1$, $X_2$, $R_2$ and $R_3$ have the meanings in each case indicated above and the rings A and B can be substituted as indicated immediately above.

The invention relates in particular to compounds of the formula Ia and their salts in which $X_2$ is lower alkylene or lower alkylidene which is unsubstituted or substituted by hydroxyl or 3- to 7-membered cycloalkyl, where a C atom of lower alkylene or lower alkylidene can be bridged by $C_2$–$C_6$alkylene, in particular $C_4$–$C_5$alkylene, or in which $X_2$ is $C_3$–$C_7$cycloalkylene, and the variables $R_1$, $X_1$, $R_2$ and $R_3$ have the meanings in each case indicated above and the rings A and B can be substituted as indicated immediately above.

The invention relates in particular to compounds of the formula Ia and their salts in which $X_2$ is the group of the formula

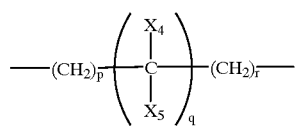

in which p is 0 or 1, q is 1 and r is 0 or 1 or in which p is 1 to 8 and q and r are in each case 0; $X_4$ is lower alkyl or phenyl which is unsubstituted or substituted by hydroxyl, 3- to 7-membered cycloalkyl, phenyl or imidazolyl and $X_5$ is hydrogen or lower alkyl; $R_2$ is carboxyl, lower alkoxycarbonyl, phenyl-lower alkoxycarbonyl, lower alkoxy-lower alkoxycarbonyl, hydroxyl, lower alkoxy, phenyl-lower alkoxy, phenoxy, amino, lower alkanoylamino, phenyl-lower alkanoylamino or lower alkanesulfonylamino; and the variables $R_1$, $X_1$ and $R_3$ have the meanings in each case indicated above; where (hetero) aromatic radicals including the rings A and B are in each case unsubstituted or substituted by halogen, trifluoromethyl, hydroxyl, lower alkoxy, lower alkyl or hydroxy-lower alkyl.

The invention relates in particular to compounds of the formula Ia and their salts in which $X_2$ is the group of the formula Ib in which p is 0 or 1, q is 1 and r is 0 or 1 or in which p is 1 to 8 and q and r are in each case 0; $X_4$ is lower alkyl or phenyl which is unsubstituted or substituted by hydroxyl, 3- to 7-membered cyclohexyl, phenyl or imidazolyl and $X_5$ is hydrogen or lower alkyl; or $X_4$ and $X_5$ together are $C_2$–$C_6$alkylene, in particular $C_4$–$C_5$alkylene, or $X_2$ is $C_3$–$C_7$cycloalkylene, in particular $C_5$–$C_6$cycloalkylene; $R_2$ is carboxyl, lower alkoxycarbonyl, phenyl-lower alkoxycarbonyl, lower alkoxy-lower alkoxycarbonyl, hydroxyl, lower alkoxy, phenyl-lower alkoxy, phenoxy, amino, lower alkanoylamino, phenyl-lower alkanoylamino or lower alkanesulfonylamino; and the variables $R_1$, $X_1$ and $R_3$ have the meanings in each case indicated above; where (hetero)aromatic radical (sic) including the rings A and B are in each case unsubstituted or substituted by halogen, trifluoromethyl, hydroxyl, lower alkoxy, lower alkyl or hydroxy-lower alkyl.

The invention relates in particular to compounds of the formula Ia and their salts in which $R_1$ is lower alkyl, in particular $C_3$–$C_5$alkyl, or lower alkenyl, in particular $C_3$–$C_5$alkenyl; $X_1$ is CO or also $SO_2$; $X_2$ is the group of the formula Ib in which p and r are 0 or 1 and q is 1; $X_4$ is lower alkyl, in particular $C_1$–$C_4$alkyl, which is unsubstituted or substituted by hydroxyl, 3- to 7-membered cycloalkyl, such as cyclohexyl, or by phenyl or imidazolyl which is unsubstituted or substituted by halogen or hydroxyl, such as 4-imidazolyl, or is phenyl; $X_5$ is hydrogen or lower alkyl, such as $C_1$–$C_4$alkyl, or $X_4$ and $X_5$ together are $C_2$–$C_6$alkylene, such as $C_4$–$C_5$alkylene, or $X_2$ is $C_3$–$C_7$cycloalkylene, such as $C_5$–$C_6$cycloalkylene, such as 1,4-cyclohexylene; $R_2$ is carboxyl, lower alkoxycarbonyl, such as $C_2$–$C_5$alkoxycarbonyl, phenyl-lower alkoxycarbonyl, such as phenyl-$C_1$–$C_4$alkoxycarbonyl, lower alkoxy-lower alkoxycarbonyl, such as $C_1$–$C_4$alkoxy-$C_2$–$C_5$alkoxycarbonyl, hydroxyl or lower alkoxy, such as $C_1$–$C_4$alkoxy; $R_3$ is carboxyl or 5-tetrazolyl; where (hetero) aromatic radical (sic) including the rings A and B are in each case unsubstituted or substituted by halogen, trifluoromethyl, hydroxyl, lower alkoxy, lower alkyl or hydroxy-lower alkyl.

The invention relates in particular to compounds of the formula Ia and their salts in which $R_1$ is lower alkyl, in particular $C_3$–$C_5$alkyl, or lower alkenyl, in particular $C_3$–$C_5$alkenyl; $X_1$ is CO or also $SO_2$; $X_2$ is the group of the formula Ib in which p and r are 0 or 1 and q is 1; $X_4$ is lower alkyl, in particular $C_1$–$C_4$alkyl, which is unsubstituted or substituted by hydroxyl, 3- to 7-membered cycloalkyl, such as cyclohexyl, or by phenyl or imidazolyl which is unsubstituted or substituted by halogen or hydroxyl, such as 4-imidazolyl, or is phenyl; $X_5$ is hydrogen or lower alkyl, such as $C_1$–$C_4$alkyl; $R_2$ is carboxyl, lower alkoxycarbonyl, such as $C_2$–$C_5$alkoxycarbonyl, phenyl-lower alkoxycarbonyl, such as phenyl-$C_1$–$C_4$alkoxycarbonyl, lower alkoxy-lower alkoxycarbonyl, such as $C_1$–$C_4$alkoxy-$C_2$–$C_5$alkoxycarbonyl, hydroxyl or lower alkoxy, such as $C_1$–$C_4$alkoxy; $R_3$ is carboxyl or 5-tetrazolyl; where (hetero) aromatic radical (sic) including the rings A and B are in each case unsubstituted or substituted by halogen, trifluoromethyl, hydroxyl, lower alkoxy, lower alkyl or hydroxy-lower alkyl.

The invention relates in particular to compounds of the formula Ia and their salts in which $R_1$ is lower alkyl, in particular $C_3$–$C_5$alkyl, or also lower alkenyl, in particular $C_3$–$C_5$alkenyl; $X_1$ is CO or also $SO_2$; $X_2$ is the group of the formula Ib in which p is 1–8 and q and r are 0; $R_2$ is hydroxyl, lower alkoxy, such as $C_1$–$C_4$alkoxy, phenyl-lower alkoxy, such as phenyl-$C_1$–$C_4$alkoxy, phenoxy, lower alkanoylamino, such as $C_1$–$C_4$alkanoylamino, phenyl-lower alkanoylamino, such as phenyl-$C_1$–$C_4$alkanoylamino, or lower alkanesulfonylamino, such as $C_1$–$C_4$alkanesulfonylamino; $R_3$ is carboxyl or primarily 5-tetrazolyl; where (hetero)aromatic radicals including the rings A and B are in each case unsubstituted or substituted by halogen, trifluoromethyl, hydroxyl, lower alkoxy, lower alkyl or hydroxy-lower alkyl.

The invention relates primarily to compounds of the formula Ia and their salts in which $R_1$ is $C_3$–$C_5$alkyl or secondarily $C_3$–$C_5$alkenyl; $X_1$ is CO or also $SO_2$; $X_2$ is the group of the formula Ib in which p and r independently of one another are 0 or 1; $X_4$ is $C_1$–$C_4$alkyl, such as methyl, ethyl, propyl, isopropyl, 1- or 2-butyl, hydroxy-$C_1$–$C_4$alkyl, such as hydroxymethyl, $C_3$–$C_7$cycloalkyl-$C_1$–$C_4$alkyl, such as cyclohexylmethyl, phenyl-$C_1$–$C_4$alkyl, such as benzyl, or imidazolyl-$C_1$–$C_4$alkyl, such as imidazol-4-ylmethyl; $X_5$ is hydrogen or $C_1$–$C_4$alkyl, such as methyl; or $X_4$ and $X_5$ together are tetramethylene or also pentamethylene; $R_2$ is carboxyl or $C_2$–$C_5$alkoxycarbonyl or also phenyl-$C_1$–$C_4$alkoxycarbonyl, such as benzyloxycarbonyl; $R_3$ is carboxyl or in particular 5-tetrazolyl.

The invention relates primarily to compounds of the formula Ia and their salts in which $R_1$ is $C_3$–$C_5$alkyl or secondarily $C_3$–$C_5$alkenyl; $X_1$ is CO or also $SO_2$; $X_2$ is the group of the formula Ib in which p and r in each case are 0 or 1 and q is 1; $X_4$ is $C_1$–$C_4$alkyl, such as methyl, ethyl, propyl, isopropyl, or 1- or 2-butyl, hydroxy-$C_1$–$C_4$alkyl, such as hydroxymethyl, $C_3$–$C_7$cycloalkyl-$C_1$–$C_4$alkyl, such as cyclohexylmethyl, phenyl-$C_1$–$C_4$alkyl, such as benzyl, or imidazolyl-$C_1$–$C_4$alkyl, such as imidazol-4-ylmethyl; $X_5$ is hydrogen; $R_2$ is carboxyl or $C_2$–$C_5$alkoxycarbonyl, or also phenyl-$C_1$–$C_4$alkoxycarbonyl, such as benzyloxycarbonyl; $R_3$ is carboxyl or 5-tetrazolyl.

The invention relates primarily to compounds of the formula Ia and their salts in which $R_1$ is $C_3$–$C_5$alkyl, such as propyl, butyl or pentyl; $X_1$ is CO; $X_2$ is the group of the formula Ib in which q and r are 0 and p is 1 to 3, in particular 2, or in which p and q are 1 and r is 0; $X_4$ is $C_1$–$C_4$alkyl, such as methyl, ethyl, propyl, isopropyl, or 1- or 2-butyl; $X_5$ is hydrogen or $C_1$–$C_4$alkyl, such as methyl; $R_2$ is carboxyl or $C_2$–$C_5$alkoxycarbonyl, such as methoxy- or ethoxycarbonyl; $R_3$ is carboxyl or 5-tetrazolyl.

The invention relates primarily to compounds of the formula Ia and their salts in which $R_1$ is $C_3$–$C_5$alkyl, such as propyl, butyl or pentyl; $X_1$ is CO; $X_2$ is the group of the formula Ib in which p is 0 or 1, r is 0 and q is 1 ; $X_4$ is $C_1$–$C_4$alkyl, such as methyl, ethyl, propyl, isopropyl, or 1- or 2-butyl; $X_5$ is hydrogen or $C_1$–$C_4$alkyl, such as methyl or ethyl, or $X_4$ and $X_5$ together are tetramethylene or pentamethylene; $R_2$ is carboxyl or $C_2$–$C_5$alkoxycarbonyl, such as methoxy- or ethoxycarbonyl; $R_3$ is 5-tetrazolyl.

The invention relates primarily to compounds of the formula Ia and their salts in which $R_1$ is $C_3$–$C_5$alkyl, such as propyl, butyl or pentyl; $X_1$ is CO; $X_2$ is the group of the formula Ib in which p is 0 or 1 and r is 0 and q is 1; $X_4$ and $X_5$ together are tetramethylene or also pentamethylene; $R_2$ is carboxyl or $C_2$–$C_5$alkoxycarbonyl, such as methoxy- or ethoxycarbonyl; $R_3$ is 5-tetrazolyl.

The invention relates primarily to compounds of the formula Ia and their salts in which $R_1$ is $C_3$–$C_5$alkyl, such as propyl, butyl or pentyl; $X_1$ is CO; $X_2$ is the group of the formula Ib in which p and r are 0 or 1 and q is 1 ; $X_4$ is $C_1$–$C_4$alkyl, such as methyl, ethyl, propyl, isopropyl, or 1- or 2-butyl; $X_5$ is hydrogen; $R_2$ is carboxyl or $C_2$–$C_5$alkoxycarbonyl, such as methoxy- or ethoxycarbonyl; $R_3$ is 5-tetrazolyl.

The invention relates in particular to the novel compounds shown in the examples and to the modes of preparation described therein.

The invention relates to processes for the preparation of the compounds according to the invention. The preparation of compounds of the formula Ia and their salts is carried out in a manner known per se and comprises, for example, a) in a compound of the formula

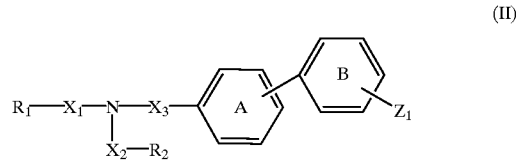

(II)

or a salt thereof in which $Z_1$ is a radical which can be converted into $R_3$, converting $Z_1$ into $R_3$, or b) reacting a compound of the formula R$_1$-X$_1$OH (IIIa), a reactive derivative thereof or a salt thereof with a compound of the formula

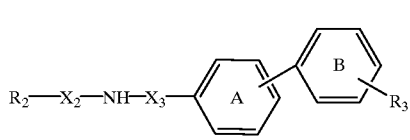

(IIIb)

or a salt thereof, and, if desired, converting a compound of the formula I or a salt thereof obtainable according to the process or in another manner into another compound according to the invention or a salt thereof, converting a free compound of the formula I obtainable according to the process into a salt, converting a salt obtainable according to the process into the free compound of the formula I or into another salt, or separating a mixture of isomers obtainable according to the process and isolating the desired compound.

Salts of starting materials which have at least one basic centre, for example of the formula IIIb, are appropriate acid addition salts, while salts of starting materials which have an acidic group, for example of the formula (IIIa), are present as salts with bases, in each case as mentioned above in connection with corresponding salts of the formula I.

Z$_1$ radicals which can be converted into the variable R$_3$ are, for example, cyano, mercapto, halogen, the group —N$_2$$^+$A$^-$, in which A$^-$ is an anion derived from an acid, amino and various functionally modified forms of COOH, SO$_3$H, PO$_3$H$_2$ or PO$_2$H$_2$ as well as N-protected 5-tetrazolyl.

Reactive derivatives of compounds of the formula IIIa are, for example, activated esters or reactive anhydrides derived therefrom, and also reactive cyclic amides.

The reactions described above and below in the variants are carried out in a manner known per se, for example in the absence or, customarily, in the presence of a suitable solvent or diluent or a mixture thereof, the reaction, as required, being carried out with cooling, at room temperature or with warming, for example in a temperature range from about −80° C. up to the boiling point of the reaction medium, preferably from about −10° to about +200° C., and, if necessary, in a closed vessel, under pressure, in an inert gas atmosphere and/or under anhydrous conditions.

Process variant a

Z$_1$, radicals which can be converted into 5-tetrazolyl R$_3$ are, for example, cyano or protected 5-tetrazolyl.

To prepare compounds of the formula I in which R$_3$ is 5-tetrazolyl, a starting material of the formula II, for example, is used in which Z$_1$, is cyano, and this is reacted with an azide, such as HN$_3$ or in particular a salt, such as an alkali metal salt, thereof or with an organotin azide, such as tri(lower)alkyl- or triaryltin azide. Preferred azides are, for example, sodium azide and potassium azide and also tri-C$_1$–C$_4$alkyl azide, for example triethyl- or tributyltin azide, and triphenyltin azide. Preferably, the tetrazol-5-yl formation is carried out with those compounds of the formula II in which R$_2$ is different from carboxyl.

Suitable protecting groups for protected 5-tetrazolyl are the protecting groups customarily used in tetrazole chemistry, in particular triphenylmethyl, benzyl which is unsubstituted or substituted, for example by nitro, such as 4-nitrobenzyl, lower alkoxymethyl, such as methoxy- and ethoxyethyl (sic), lower alkylthiomethyl, such as methylthiomethyl, silyl, such as tri-lower alkylsilyl, for example dimethyl-tert-butyl- and triisopropylsilyl, and 2-cyanoethyl, also lower alkoxy-lower alkoxymethyl, such as 2-methoxyethoxymethyl, benzyloxymethyl and phenacyl.

The protecting groups are removed using known methods, for example as described in J. Green, Protective Groups in Organic Synthesis, Wiley-Interscience (1980). Thus, for example, the triphenylmethyl group is customarily removed by hydrolysis, in particular in the presence of an acid, or hydrogenolysis in the presence of a hydrogenation catalyst, 4-nitrobenzyl is removed, for example, by hydrogenolysis in the presence of a hydrogenation catalyst, methoxy- or ethoxyethyoxy (sic) is removed, for example, by treating with a tri-lower alkyltin bromide, such as triethyl- or tributyltin bromide, methylthiomethyl is removed, for example, by treating with trifluoroacetic acid, silyl radicals are removed, for example, by treating with fluorides, such as tetra-lower alkylammonium fluorides, for example tetrabutylammonium fluoride, or alkali metal fluorides, for example sodium fluoride, or 2-cyanoethyl is removed, for example, by hydrolysis, for example with sodium hydroxide solution, 2-methoxyethoxymethyl is removed, for example, by hydrolysis, for example with hydrochloric acid, and benzyloxymethyl and phenacyl are removed, for example, by hydrogenolysis in the presence of a hydrogenation catalyst.

A radical which can be converted into SO$_3$H=R$_3$ is, for example, the mercapto group. Starting compounds of the formula II containing a group of this type are, for example, oxidised by oxidation processes known per se to give those compounds of the formula I in which R$_3$ is SO$_3$H. Suitable oxidising agents are, for example, inorganic peracids, such as peracids of mineral acids, for example periodic acid or persulfuric acid, organic peracids, such as appropriate percarboxylic or persulfonic acids, for example performic, peracetic, trifluoroperacetic or perbenzoic acid or p-toluenesulfonic acid (sic), or mixtures of hydrogen peroxide and acids, for example a mixture of hydrogen peroxide with acetic acid.

The oxidation is commonly carried out in the presence of suitable catalysts, suitable acids, such as substituted or unsubstituted carboxylic acids, for example acetic acid or trifluoroacetic acid, or transition metal oxides, such as oxides of elements of sub-group VII, for example vanadium oxide, molybdenum oxide or tungsten oxide, being mentioned as catalysts. The oxidation is carried out under mild conditions, for example at temperatures from about −50° to about +100° C.

A group which can be converted into PO$_3$H$_2$=R$_3$ is to be understood as meaning, for example, a group N$_2$$^+$A$^-$, in which A$^-$ is an anion of an acid, such as a mineral acid. Diazonium compounds of this type are, for example, reacted in a manner known per se with a P(III) halide, such as PCl$_3$ or PBr$_3$, and worked up by hydrolysis, those compounds of the formula I being obtainable in which R$_3$ is PO$_3$H$_2$.

A suitable Z$_1$ radical which can be converted into haloalkylsulfamoyl R$_3$ is, for example, primary amino.

In order to prepare compounds of the formula I in which R$_3$ is haloalkylsulfamoyl, corresponding anilines, for example, are reacted with a customarily reactive esterified haloalkylsulfonic acid, the reaction being carried out, if desired, in the presence of a base. A suitable preferred reactive esterified halosulfonic acid is the corresponding halide, such as a chloride or bromide.

A radical Z$_1$ which can be converted into COOH=R$_3$ is, for example, a functionally modified carboxyl, such as cyano, esterified or amidated carboxyl, hydroxymethyl or formyl.

Esterified carboxyl is, for example, carboxyl esterified with a substituted or unsubstituted aliphatic, cycloaliphatic or aromatic alcohol. An aliphatic alcohol is, for example, a lower alkanol, such as methanol, ethanol, propanol, isopropanol, n-butanol, sec- or tert-butanol, while a suitable cycloaliphatic alcohol is, for example, a 3- to 8-membered cycloalkanol, such as cyclopentanol, -hexanol or -heptanol. An aromatic alcohol is, for example, a phenol or heterocyclic alcohol, which may in each case be substituted or unsubstituted, in particular hydroxypyridine, for example 2-, 3- or 4-hydroxypyridine. Carboxyl can also be esterified with a silylated alcohol and is in particular tri-$(C_1-C_4)$alkylsilyl-$(C_1-C_4)$alkoxy carbonyl, in particular trimethylsilylethoxycarbonyl.

Amidated carboxyl is, for example, carbamoyl, carbamoyl which is monosubstituted by hydroxyl, amino, amino (sic) or substituted or unsubstituted phenyl, carbamoyl which is mono- or disubstituted by lower alkyl or carbamoyl which is disubstituted by 4- to 7-membered alkylene or 3-aza-, 3-lower alkylaza-, 3-oxo- or 3-thiaalkylene. Examples which may be mentioned are carbamoyl, N-mono- or N,N-di-lower alkylcarbamoyl, such as N-methyl-, N-ethyl-, N,N-dimethyl-, N,N-diethyl- or N,N-dipropylcarbamoyl, pyrrolidino- or piperidinocarbonyl, morpholino-, piperazino- or 4-methylpiperazino- and also thiomorpholinocarbonyl, anilinocarbonyl or anilinocarbonyl substituted by lower alkyl, lower alkoxy and/or halogen.

Preferred functionally modified carboxyl is, for example, lower alkoxycarbonyl, such as methoxy- or ethoxycarbonyl, tri-$(C_1-C_4)$alkylsilyl-$(C_1-C_4)$alkoxycarbonyl, in particular trimethylsilylethoxycarbonyl, or cyano. Compounds of the formula I in which $R_3$ is carboxyl can be prepared, for example, starting from compounds of the formula II in which $Z_1$ is functionally modified carboxyl, in a manner known per se, for example by hydrolysis, in particular in the presence of a base, in the case of appropriate tri-(C—C)alkylsilyl-(C—C)alkoxycarbonyl derivatives, for example, by treating with an ammonium fluoride, such as tetra-lower alkyl ammonium fluoride, for example tetra-n-butylammonium fluoride, or in the case of benzyloxycarbonyl derivatives by hydrogenolysis in the presence of a hydrogenation catalyst, or starting from those compounds of the formula II in which $Z_1$ is hydroxymethyl or formyl, by oxidation using customary oxidising agents.

. . . (sic) As oxidising agents, for example in an inert solvent, such as a lower alkanecarboxylic acid, for example acetic acid, a ketone, for example acetone, an ether, for example tetrahydrofuran, a heterocyclic aromatic, for example pyridine, or water or a mixture thereof, if necessary with cooling or warming, for example from about 0° to about 150° C. . . . (sic). Suitable oxidising agents are, for example, oxidising transition metal compounds, in particular those with elements of sub-groups I, VI or VIII. Examples which may be mentioned are: silver compounds, such as silver nitrate, silver oxide or silver picolinate, chromium compounds, such as chromium trioxide or potassium dichromate, manganese compounds, such as potassium ferrate (sic), tetrabutylammonium permanganate or benzyl (triethyl)ammonium permanganate. Other oxidising agents are, for example, suitable compounds with elements of main group IV, such as lead dioxide, or halogen-oxygen compounds, such as sodium diodate (sic) or potassium periodate.

Thus, for example, hydroxymethyl and formyl are oxidised to carboxyl $R_3$.

This variant is preferably suitable for the preparation of those compounds of the formula I in which the variables have meanings which are different from unsaturated radicals.

Suitable bases are, for example, alkali metal hydroxides, hydrides, amides, alkanolates, carbonates, triphenylmethylides, di-lower alkylamides, aminoalkylamides or lower alkylsilylamides, naphthaleneamines, lower alkylamines, basic heterocycles, ammonium hydroxides, and carbocyclic amines. Examples which may be mentioned are sodium hydroxide, sodium hydride, sodium amide, sodium methoxide, sodium ethoxide, potassium tert-butoxide, potassium carbonate, lithium triphenylmethylide, lithium diisopropylamide, potassium 3-(aminopropyl)amide, potassium bis(trimethylsilyl)amide, dimethylaminonaphthalene, di- or triethylamine, or ethyldiisopropylamine, N-methylpiperidine, pyridine, benzyltrimethylammonium hydroxide, 1,5-diazabicyclo[4.3.0]non-5-ene (DBN) and 1,8-diaza-bicyclo[5.4.0]undec-7-ene (DBU).

The starting material of the formula II is accessible, for example, by reacting a compound of the formula $R_2$—$X_2$—$NH_2$ (IIa) with a compound of the formula

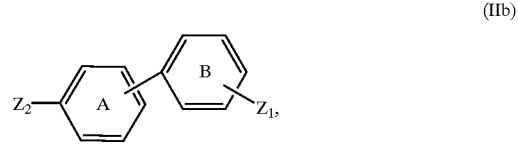

(IIb)

in which $Z_2$ is —$X_3$—$Z_4$ and $Z_4$ is reactive esterified hydroxyl, for example in the presence of a base, and reacting the compound thus obtained of the formula

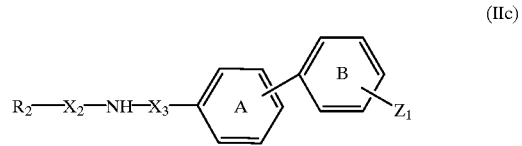

(IIc)

in the next reaction step with a compound of the formula IIIa, for example analogously to variant b).

Reactive esterified hydroxyl $Z_4$ is in particular hydroxyl esterified with a strong inorganic acid or organic sulfonic acid, for example halogen, such as chlorine, bromine or iodine, sulfonyloxy, such as hydroxysulfonyloxy, halosulfonyloxy, for example fluorosulfonyloxy, $C_1-C_7$alkanesulfonyloxy which is unsubstituted or substituted, for example by halogen, for example methane- or trifluoromethanesulfonyloxy, $C_5-C_7$cycloalkanesulfonyloxy, for example cyclohexanesulfonyloxy, or benzenesulfonyloxy which is unsubstituted or substituted, for example by $C_1-C_7$alkyl or halogen, for example p-bromobenzene- or p-toluenesulfonyloxy.

Compounds of the formula IIb, for their part, are known, for example, from EP 253,310 or can be prepared in a manner known per se. Compounds of the formula (IIa) are essentially known or are accessible analogously to preparation processes known per se.

Process variant b):

Activated esters of compounds of the formula IIIa are in particular esters which are unsaturated at the linking carbon atom of the esterifying radical, for example of the vinyl ester type, such as vinyl esters (obtainable, for example, by transesterification of an appropriate ester with vinyl acetate; activated vinyl ester method), carbamoylvinyl esters (obtainable, for example, by treating the appropriate acid with an isoxazolium reagent; 1,2-oxazolium or Woodward method) or 1-lower alkoxyvinyl esters (obtainable, for example, by treating the appropriate acid with a lower alkoxyacetylene; ethoxyacetylene method), or esters of the amidino type, such as N,N'-disubstituted amidino esters (obtainable, for example, by treating the appropriate acid with a suitable N,N'-disubstituted carbodiimide, for example N,N'-dicyclohexylcarbodiimide; carbodiimide method) or N,N-disubstituted amidino esters (obtainable, for example, by treating the appropriate acid with an N,N-disubstituted cyanamide; cyanamide method), suitable aryl esters, in particular phenyl esters substituted by electron-attracting substituents (obtainable, for example, by treating the appropriate acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensing agent, such as N,N'-dicyclohexylcarbodiimide; activated aryl ester method), cyanomethyl esters (obtainable, for example, by treating the appropriate acid with chloroacetonitrile in the presence of a base; cyanomethyl ester method), thio esters, in particular phenylthio esters which are unsubstituted or substituted, for example by nitro, (obtainable, for example, by treating the appropriate acid with thiophenols which are unsubstituted or substituted, for example by nitro, inter alia with the aid of the anhydride or carbodiimide method; activated thiol ester method) or in particular amino or amido esters (obtainable, for example, by treating the appropriate acid with an N-hydroxyamino or N-hydroxyamido compound and their activated derivatives, for example N-hydroxysuccinimide, N-hydroxypiperidine, N-hydroxyphthalimide, N-hydroxy-5-norbornene- or norbonane-2,3-dicarboximide, 1-hydroxybenzotriazole or benzotriazol-1-yloxyphosphonium salts or benzotriazol-1-yluronium salts, or 3-hydroxy-3,4-dihydro-1,2,3-benzotriazin-4-one, for example by the anhydride or carbodiimide method; activated N-hydroxy ester method).

Anhydrides of acids can be symmetrical or preferably mixed anhydrides of these acids, for example anhydrides with inorganic acids, such as acid halides, in particular acid chlorides, (obtainable, for example, by treating the appropriate acid with thionyl chloride, phosphorus pentachloride or oxalyl chloride; acid chloride method), azides (obtainable, for example, from an appropriate acid ester via the corresponding hydrazide and its treatment with nitrous acid; azide method), anhydrides with carbonic acid half-esters, for example lower alkyl carbonate half-esters (obtainable, for example, by treating the appropriate acid with lower alkyl chloroformates or with a 1-lower alkoxycarbonyl-2-lower alkoxy-1,2-dihydroquinoline, for example 1-ethoxycarbonyl-2-ethoxy-1,2-dihydroquinoline; mixed O-alkylcarbonic anhydride method), anhydrides with dihalogenated, in particular dichlorinated, phosphoric acid (obtainable, for example, by treating the appropriate acid with phosphorus oxychloride; phosphorus oxychloride method), anhydrides with other phosphoric acid derivatives (for example those which can be obtained with phenyl N-phenylphosphoramidochloridate) or with phosphorus acid derivatives, or anhydrides with organic acids, such as mixed anhydrides with organic carboxylic acids (obtainable, for example, by treating the appropriate acid with a substituted or unsubstituted lower alkane- or phenyl-lower alkane carbonyl halide, for example phenylacetyl, pivaloyl or trifluoroacetyl chloride; mixed carbonic anhyride method) or with organic sulfonic acids (obtainable, for example, by treating a salt, such as an alkali metal salt, of the appropriate acid with a suitable organic sulfonyl halide, such as lower alkane- or arylsufonyl chloride, for example methane- or p-toluenesulfonyl chloride; mixed sulfonic anhydride method), and also symmetrical anhydrides (obtainable, for example, by condensation of the appropriate acid in the presence of a carbodiimide or of 1-diethylaminopropyne; symmetrical anhyride (sic) method).

Suitable cyclic amides are in particular amides having five-membered diazacyclic compounds of aromatic character, such as amides with imidazoles, for example imidazole (obtainable, for example, by treating the appropriate acid with N,N'-carbonyldiimidazole; imidazole method), or pyrazoles, for example 3,5-dimethylpyrazole (obtainable, for example, via the acid hydrazide by treating with acetylacetone; pyrazolide method).

The condensation reaction for the preparation of the amide compound can be carried out in a manner known per se, for example as described in standard texts, such as "Houben-Weyl, Methoden der organischen Chemie" (sic) (Methods of Organic Chemistry), 4th edition, Volume 15/II, Georg Thieme Verlag, Stuttgart 1974, "The Peptides" (editors E. Gross and J. Meienhofer), Volumes 1 and 2, Academic Press, London and New York, 1979/1980, or M. Bodanszky, "Principles of Peptide Synthesis", Springer-Verlag, Berlin 1984.

The condensation reaction can be carried out in the presence of one of the customary condensing agents. Customary condensing agents are, for example, carbodiimides, for example diethyl-, dipropyl- or N-ethyl-N'-(3-dimethylaminopropyl)carbodiimide or in particular dicyclohexylcarbodiimide, and also suitable carbonyl compounds, for example carbonyldiimidazole, 1,2-oxazolium compounds, for example 2-ethyl-5-phenyl-1,2-oxazolium-3'-sulfonate and 2-tert-butyl-5-methylisoxazolium perchlorate, or a suitable acylamino compound, for example 2-ethoxy-1-ethoxycarbonyl-1,2-dihydroquinoline, and also activated phosphoric acid derivatives, for example diphenylphosphoryl azide, diethylphosphoryl cyanide, phenyl N-phenylphosphoramidochloridates, bis(2-oxo-3-oxazolidinyl)phosphinoyl chloride or 1-benzotriazolyloxy-tris(dimethylamino)phosphonium hexafluorophosphate.

If desired, an organic base is added, for example a tri-lower alkylamine having bulky radicals, for example ethyldiisopropylamine, or a heterocyclic base, for example pyridine, 4-dimethylaminopyridine or preferably N-methylmorpholine.

The condensation of acid anhydrides with amines can be carried out, for example, in the presence of inorganic carbonates, for example alkali metal carbonates or hydrogencarbonates, such as sodium or potassium carbonate or hydrogencarbonate (customarily together with a sulfate).

The condensation reaction is preferably carried out in an inert polar aprotic, preferably anhydrous, solvent or solvent mixture, for example in a carboxamide, for example formamide or dimethylform amide, a halogenated hydrocarbon, for example methylene chloride, carbon tetrachloride or chlorobenzene, a ketone, for example acetone, cyclic ethers, for example tetrahydrofuran, an ester, for example ethyl acetate, or a nitrile, for example acetonitrile, or in mixtures thereof, if desired at reduced or elevated temperature, for example in a temperature range from about −40° C. to about +100° C., preferably from about −10° C. to about +50° C., and if desired under an inert gas atmosphere, for example a nitrogen atmosphere.

Reactive acid derivatives can also be formed in situ.

The starting material of the formula IIIb can be prepared, for example, by reacting a compound of the formula IIa with a compound of the formula

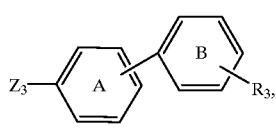
(IIIc)

in which $Z_3$ is —$X_3$—$Z_4$ and $Z_4$ is reactive esterified hydroxyl, in particular in the presence of one of the above-mentioned bases. To prepare compounds of the formula IIIb in which $X_3$ is —$CH_2$—, compounds of the formula IIa, for example, are used as starting materials and these are reacted with compounds of the formula IIIc in which $Z_3$ is formyl. The Schiff's bases obtainable in this way are then reduced with the aid of a reducing agent, such as sodium cyanoborohydride.

Reactive esterified hydroxyl $Z_4$ is in particular hydroxyl esterified with a strong inorganic acid or organic sulfonic acid, for example halogen, such as chlorine, bromine or iodine, sulfonyloxy, such as hydroxysulfonyloxy, halosulfonyloxy, for example fluorosulfonyloxy, $C_1$–$C_7$ alkanesulfonyloxy which is unsubstituted or substituted, for example by halogen, for example methane- or trifluoromethanesulfonyloxy, $C_5$–$C_7$ cycloalkanesulfonyloxy, for example cyclohexanesulfonyloxy, or benzenesulfonyloxy which is unsubstituted or substituted, for example by $C_1$–$C_7$ alkyl or halogen, for example p-bromobenzene- or p-toluenesulfonyloxy.

A compound according to the invention which is obtainable by the process can be converted into another compound according to the invention in a manner known per se.

A compound according to the invention containing hydroxyl can be etherified by methods known per se. The etherification can be carried out, for example, using an alcohol, such as a substituted or unsubstituted lower alkanol, or a reactive ester thereof. Suitable reactive esters of the desired alcohols are, for example, those with strong inorganic or organic acids, such as corresponding halides, sulfates, lower alkanesulfonates or substituted or unsubstituted benzenesulfonates, for example chlorides, bromides, iodides, methane-, benzene- or p-toluenesulfonates. The etherification can be carried out, for example, in the presence of a base, an alkali metal hydride, hydroxide or carbonate, or of an amine. Conversely, corresponding ethers, such as lower alkoxy compounds, can be cleaved, for example, by means of strong acids, such as mineral acids, for example the hydrohalic acids hydrobromic or hydriodic acid, which may advantageously be present in the form of pyridinium halides, or by means of Lewis acids, for example halides of elements of main group III or the corresponding sub-groups. These reactions can be carried out, if necessary, with cooling or warming, for example in a temperature range from about –20° to about 100° C., in the presence or absence of a solvent or diluent, under inert gas and/or under pressure and, if appropriate, in a closed vessel.

Compounds according to the invention containing hydroxymethyl groups can be prepared, for example, starting from compounds containing corresponding carboxyl or esterified carboxyl, corresponding compounds being reduced in a manner known per se, for example by reduction with a hydride which, if desired, may be complex, such as a hydride formed from an element of the 1st and 3rd main groups of the periodic table of the elements, for example borohydride or aluminohydride, for example lithium borohydride, lithium aluminium hydride, diisobutylaluminium hydride (an additional reduction step using alkal (sic) metal cyanoborohydride, such as sodium cyanoborohydride, may be necessary), and also diborane.

If an aromatic structural component is substituted by (lower) alkylthio (in $S(O)_m$—R m is 0), this can be oxidised in a customary manner to corresponding (lower) alkanesulfmyl or -sulfonyl. Suitable oxidising agents for the oxidation to the sulfoxide step are, for example, inorganic peracids, such as peracids of mineral acids, for example periodic acid or persulfuric acid, organic peracids, such as appropriate percarboxylic or persulfonic acids, for example performic, peracetic, trifluoroperacetic or perbenzoic acid or p-toluenepersulfonic acid, or mixtures of hydrogen peroxide and acids, for example a mixture of hydrogen peroxide with acetic acid.

The oxidation is commonly carried out in the presence of suitable catalysts, catalysts which can be mentioned being suitable acids, such as substituted or unsubstituted carboxylic acids, for example acetic acid or trifluoroacetic acid, or transition metal oxides, such as oxides of elements of sub-group VII, for example vanadium oxide, molybdenum oxide or tungsten oxide. The oxidation is carried out under mild conditions, for example at temperatures from about –50° to about +100° C.

The oxidation to the sulfone step may also be carried out appropriately at low temperatures using dinitrogen tetroxide as the catalyst in the presence of oxygen, just like the direct oxidation of (lower) alkylthio to (lower) alkanesulfonyl. However, in this case the oxidising agent is customarily employed in an excess.

If one of the variables contains amino, corresponding compounds of the formula I, their tautomers or salts can be N-alkylated in a manner known per se; likewise, carbamoyl or radicals containing carbamoyl can be N-alkylated. The (aryl)alkylation is carried out, for example, using a reactive ester of an (aryl)$C_1$–$C_7$alkyl halide, for example a bromide or iodide, (aryl)$C_1$–$C_7$alkylsulfonate, for example methanesulfonate or p-toluenesulfonate, or a di-$C_1$–$C_7$alkyl sulfate, for example dimethyl sulfate, preferably under basic conditions, such as in the presence of sodium hydroxide solution or potassium hydroxide solution, and advantageously in the presence of a phase transfer catalyst, such as tetrabutylammonium bromide or benzyltrimethylammonium chloride, where, however, stronger basic condensing agents, such as alkali metal amides, hydrides or alkoxides, for example sodium amide, sodium hydride or sodium ethoxide, may be necessary. Amino can also be acylated in a manner known per se, for example analogously to variant b).

In compounds of the formula I which contain an esterified or amidated carboxyl group as a substituent, a group of this type can be converted into a free carboxyl group, for example by means of hydrolysis, for example in the presence of a basic agent, or of an acidic agent, such as a mineral acid. Tert-butyloxycarbonyl, for example, can furthermore be converted into carboxyl, for example in a manner known per se, such as treating with trihaloacetic acid, such as trifluoroacetic acid, and benzyloxycarbonyl can be converted into carboxyl, for example by catalytic hydrogenation in the presence of a hydrogenation catalyst, for example in the manner described below.

Furthermore, in compounds of the formula I which contain a carboxyl group as a substituent, in particular if $R_3$ is different from carboxyl, this can be converted into an esterified carboxyl group, for example, by treating with an alcohol, such as a lower alkanol, in the presence of a suitable esterifying agent, such as an acid reagent, for example an inorganic or organic acid or a Lewis acid, for example zinc chloride, or a condensing agent which binds water, for example a carbodiimide, such as N,N'-dicyclohexylcarbodiimide, or by treating with a diazo reagent, such as with a diazo-lower alkane, for example diazomethane. This can also be obtained if compounds of the formula I in which the carboxyl group is present in free form or in salt form, such as ammonium salt or metal salt form, for example alkali metal salt form, such as sodium salt or potassium salt form, are treated with a reactive ester of a ($C_1$–$C_7$)alkyl halide, for example methyl or ethyl bromide or iodide, or an organic sulfonic acid ester, such as an appropriate ($C_1$–$C_7$)alkyl ester, for example methyl or ethyl methanesulfonate or p-toluenesulfonate.

Compounds of the formula I which contain an esterified carboxyl group as a substituent can be transesterified into other ester compounds of the formula I by transesterification, for example by treating with an alcohol, customarily a higher appropriate alcohol than that of the esterified carboxyl group in the starting material, in the presence of a suitable transesterifying agent, such as a basic agent, for example an alkali metal ($C_1$–$C_7$)alkanoate, ($C_1$–$C_7$)alkanolate or alkali metal cyanide, such as sodium acetate, sodium methoxide, sodium ethoxide, sodium tert-butoxide or sodium cyanide, or a suitable acid agent, if appropriate with removal of the resulting alcohol, for example by distillation. Appropriate, so-called activated esters of the formula I which contain an activated esterified carboxyl group as a substituent may also be used as starting materials (see below), and these may be converted into another ester by treating with a ($C_1$–$C_7$)alkanol.

In compounds of the formula I which contain the carboxyl group as a substituent, this can also first be converted into a reactive derivative, such as an anhydride, including a mixed anhydride, such as an acid halide, for example an acid chloride (for example by treating with a thionyl halide, for example thionyl chloride), or an anhydride using a formic acid ester, for example a ($C_1$–$C_7$)alkyl ester (for example by treating a salt, such as an ammonium or alkali metal salt, with a haloformic acid ester, such as a chloroformic acid ester, such as a ($C_1$–$C_7$)alkyl ester), or into an activated ester, such as a cyanomethyl ester, a nitrophenyl ester, for example a 4-nitrophenyl ester, or a polyhalophenyl ester, for example a pentachlorophenyl ester (for example by treating with an appropriate hydroxyl compound in the presence of a suitable condensing agent, such as N,N'-dicyclohexylcarbodiimide), and then a reactive derivative of this type can be reacted with an amine and in this way amide compounds of the formula I which contain an amidated carboxyl group as a substituent can be obtained. In this case, these can be obtained directly or via intermediate compounds; thus, for example, an activated ester, such as a 4-nitrophenyl ester, of a compound of the formula I containing a carboxyl group can first be reacted with a 1-unsubstituted imidazole and the 1-imidazolylcarbonyl compound obtained in this way brought to reaction with an amine. However, other nonactivated esters, such as ($C_1$–$C_7$)alkyl esters of compounds of the formula I, which contain, for example, ($C_2$–$C_8$) alkoxycarbonyl as a substituent, can also be brought to reaction with amines.

If an aromatic ring contains a hydrogen atom as a substituent, the latter can be replaced by a halogen atom with the aid of a halogenating agent in a customary manner, for example brominated with bromine, hypobromic acid, acyl hypobromites or other organic bromine compounds, for example N-bromosuccinimide, N-bromoacetamide, N-bromophthalimide, pyridinium perbromide, dioxane dibromide, 1,3-dibromo-5,5-dimethylhydantoin or 2,4,4,6-tetrabromo-2,5-cyclohexanedien-1-one, or chlorinated with elemental chlorine, for example in a halogenated hydrocarbon, such as chloroform, and with cooling, for example from down to about −10° to about +100° C.

If an aromatic ring in the compounds according to the invention contains an amino group, this can be diazotized in a customary manner, for example by treating with a nitrite, for example sodium nitrite, in the presence of a suitable protonic acid, for example a mineral acid, the reaction temperature advantageously- being kept below about 5° C. The diazonium group present in the salt form and obtainable in this way can be substituted by analogous processes, for example as follows: by the hydroxyl group analogously to the boiling-out of phenol in the presence of water, by an alkoxy group by treating with an appropriate alcohol, energy having to be added; by the fluorine atom analogously to the Schiemann reaction in the thermolysis of corresponding diazonium tetrafluoroborates; by the halogen atoms chlorine, bromine or iodine and also the cyano group analogously to the Sandmeyer reaction in the reaction with corresponding Cu(I) salts, initially with cooling, for example to below about 5° C., and then heating, for example to about 60° to about 150° C.

If the compounds of the formula I contain unsaturated radicals, such as (lower) alkenyl or (lower) alkynyl groups, these can be converted into saturated radicals in a manner known per se. Thus, for example, multiple bonds are hydrogenated by catalytic hydrogenation in the presence of hydrogenation catalysts, suitable catalysts for this purpose being, for example, nickel, such as Raney nickel, and noble metals or their derivatives, for example oxides, such as palladium or platinum oxide, which may be applied, if desired, to support materials, for example to carbon or calcium carbonate. The hydrogenation may preferably be carried out at pressures between 1 and about 100 at and at room temperature between about −80° to about 200° C., in particular between room temperature and about 100° C. The reaction is advantageously carried out in a solvent, such as water, a lower alkanol, for example ethanol, isopropanol or n-butanol, an ether, for example dioxane, or a lower alkanecarboxylic acid, for example acetic acid.

Furthermore, in compounds of the formula I in which, for example, one of the radicals $R_1$ and/or $X_2$ contains halogen, such as chlorine, halogen can be replaced by reaction with a substituted or unsubstituted amine, an alcohol or a mercaptan.

The invention relates in particular to the processes described in the examples.

Salts of compounds of the formula I can be prepared in a manner known per se. Thus, for example, acid addition salts of compounds of the formula I are obtained by treating with an acid or a suitable ion exchange reagent. Salts can be converted into the free compounds in a customary manner, and acid addition salts can be converted, for example, by treating with a suitable basic agent.

Depending on the procedure and reaction conditions, the compounds according to the invention having salt-forming, in particular basic properties, can be obtained in free form or preferably in the form of salts.

In view of the close relationship between the novel compound in the free form and in the form of its salts, in the preceding text and below the free compound or its salts may correspondingly and advantageously also be understood as meaning the corresponding salts or the free compound.

The novel compounds including their salts of salt-forming compounds can also be obtained in the form of their hydrates or can include other solvents used for crystallization.

Depending on the choice of the starting materials and procedures, the novel compounds can be present in the form of one of the possible isomers or as mixtures thereof, for example as pure optical isomers, such as antipodes, or as isomer mixtures, such as racemates, diastereoisomer mixtures or racemate mixtures, depending on the number of asymmetric carbon atoms. For example, compounds of the formula Ia in which $X_2$ is the group of the formula Ib . . . (sic) is 1 and in which $X_4$ and $X_5$ have different meanings, have an asymmetric C atom. In corresponding compounds of the formula I in which $R_2$, for example, is carboxyl which, if desired, is esterified or amidated or hydroxyl which, if desired, is etherified, the asymmetric C atom of the partial structure of the formula —$X_2$—$R_2$ concerned preferably has the L-configuration.

Racemates and diastereomer mixtures obtained can be separated into the pure isomers or racemates in a known manner on the basis of the physicochemical differences of the components, for example by fractional crystallization. Racemates obtained may furthermore be resolved into the optical antipodes by known methods, for example by recrystallization from an optically active solvent, chromatography on chiral adsorbents, with the aid of suitable microorganisms, by cleavage with specific immobilized enzymes, via the formation of inclusion compounds, for example using chiral crown ethers, only one enantiomer being complexed, or by conversion into diastereomeric salts, for example by reaction of a basic final substance racemate with an optically active acid, such as a carboxylic acid, for example tartaric or malic acid, or sulfonic acid, for example camphorsulfonic acid, and separation of the diastereomer mixture obtained in this manner, for example on the basis of its differing solubilities, into the diastereomers from which the desired enantiomer can be liberated by the action of suitable agents. The more active enantiomer is advantageously isolated.

The invention also relates to those embodiments of the process, according to which a compound obtainable as an intermediate in any step of the process is used as a starting material and the missing steps are carried out or a starting material in the form of a derivative or salt and/or its racemates or antipodes is used or, in particular, formed under the reaction conditions.

In the process of the present invention, those starting materials are preferably used which lead to the compounds described as particularly useful at the beginning. The invention likewise relates to novel starting materials which have been specifically developed for the preparation of the compounds according to the invention, to their use and to processes for their preparation, the variables R, $R_1$, $R_2$, $R_3$, $X_1$, $X_2$, $X_3$, $X_4$, $X_5$, m, p, q and r having the meanings indicated for the preferred compound groups of the formula I in each case. In particular, compounds of the formula IIa, their tautomers and salts in which $Z_1$ is cyano are preferred as starting materials.

The invention likewise relates to the use of the compounds of the formula I or of pharmaceutically acceptable salts of compounds of this type with salt-forming properties, in particular as pharmacological, primarily angiotensin II antagonist, active substances. In this connection, they can be used, preferably in the form of pharmaceutically acceptable preparations, in a method for the prophylactic and/or therapeutic treatment of the animal or human body, in particular as angiotensin II antagonists.

The invention likewise relates to pharmaceutical preparations which contain the compounds according to the invention or pharmaceutically acceptable salts thereof as active ingredients, and to processes for their preparation.

The pharmaceutical preparations according to the invention which contain the compound according to the invention or pharmaceutically acceptable salts thereof are those for enteral, such as oral, furthermore rectal, and parenteral administration to (a) warm-blooded animal(s), the pharmacological active ingredient being present on its own or together with a pharmaceutically acceptable carrier. The daily dose of the active ingredient depends on the age and the individual condition and also on the manner of administration.

The novel pharmaceutical preparations contain, for example, from about 10% to about 80%, preferably from about 20% to about 60%, of the active ingredient. Pharmaceutical preparations according to the invention for enteral or parenteral administration are, for example, those in unit dose forms, such as sugar-coated tablets, tablets, capsules or suppositories, and furthermore ampoules. These are prepared in a manner known per se, for example by means of conventional mixing, granulating, sugar-coating, dissolving or lyophilizing processes. Thus, pharmaceutical preparations for oral use can be obtained by combining the active ingredient with solid carriers, if desired granulating a mixture obtained, and processing the mixture or granules, if desired or necessary, after addition of suitable excipients to give tablets or sugar-coated tablet cores.

Suitable carriers are, in particular, fillers, such as sugars, for example lactose, sucrose, mannitol or sorbitol, cellulose preparations and/or calcium phosphates, for example tricalcium phosphate or calcium hydrogen phosphate, furthermore binders, such as starch paste, using, for example, corn, wheat, rice or potato starch, gelatin, tragacanth, methylcellulose and/or polyvinylpyrrolidone, if desired, disintegrants, such as the abovementioned starches, furthermore carboxymethyl starch, crosslinked polyvinylpyrrolidone, agar, alginic acid or a salt thereof, such as sodium alginate; auxiliaries are primarily glidants, flow-regulators and lubricants, for example silicic acid, talc, stearic acid or salts thereof, such as magnesium or calcium stearate, and/or polyethylene glycol. Sugar-coated tablet cores are provided with suitable coatings which, if desired, are resistant to gastric juice, using, inter alia, concentrated sugar solutions which, if desired, contain gum arabic, talc, polyvinylpyrrolidone, polyethylene glycol and/or titanium dioxide, coating solutions in suitable organic solvents or solvent mixtures or, for the preparation of gastric juice-resistant coatings, solutions of suitable cellulose preparations, such as acetylcellulose phthalate or hydroxypropylmethylcellulose phthalate. Colorants or pigments, for example to identify or to indicate different doses of active ingredient, may be added to the tablets or sugar-coated tablet coatings.

Other orally utilizable pharmaceutical preparations are hard gelatin capsules, and also soft closed capsules made of gelatin and a plasticizer, such as glycerol or sorbitol. The hard gelatin capsules may contain the active ingredient in the form of granules, for example in a mixture with fillers, such as lactose, binders, such as starches, and/or lubricants, such as talc or magnesium stearate, and, if desired, stabilizers. In soft capsules, the active ingredient is preferably dissolved or suspended in suitable liquids, such as fatty oils, paraffin oil or liquid polyethylene glycols, it also being possible to add stabilizers.

Suitable rectally utilizable pharmaceutical preparations are, for example, suppositories, which consist of a combination of the active ingredient with a suppository base. Suitable suppository bases are, for example, natural or synthetic triglycerides, paraffin hydrocarbons, polyethylene glycols or higher alkanols. Furthermore, gelatin rectal capsules which contain a combination of the active ingredient with a base substance may also be used. Suitable base substances are, for example, liquid triglycerides, polyethylene glycols or paraffin hydrocarbons.

Suitable preparations for parenteral administration are primarily aqueous solutions of an active ingredient in water-soluble form, for example a water-soluble salt, and furthermore suspensions of the active ingredient, such as appropriate oily injection suspensions, using suitable lipophilic solvents or vehicles, such as fatty oils, for example sesame oil, or synthetic fatty acid esters, for example ethyl oleate or triglycerides, or aqueous injection suspensions which contain viscosity-increasing substances, for example sodium carboxymethylcellulose, sorbitol and/or dextran, and, if necessary, also stabilizers.

The dose of the active ingredient depends on the warm-blooded animal species, the age and the individual condition and on the manner of administration. In the normal case, an approximate daily dose of about 10 mg to about 250 mg is to be estimated in the case of oral administration for a patient weighing approximately 75 kg.

The following examples illustrate the invention described above; however, they are not intended to limit its extent in any manner. Temperatures are indicated in degrees Celsius.

The following solvent systems are used for chromatography in the examples which follow:

Neutral systems:

| N1 | Ethyl acetate-hexane | 2-1 |
| N2 | Ethyl acetate-hexane | 1-1 |
| N3 | Ethyl acetate-hexane | 1-2 |
| N4 | Ethyl acetate-hexane | 1-4 |
| N5 | Ethyl acetate-hexane | 1-9 |
| N6 | Methylene chloride-methanol | 95-5 |
| N7 | Methylene chloride-methanol | 9-1 |
| N8 | Methylene chloride-methanol | 4-1 |
| N9 | Methylene chloride-methanol | 2-1 |
| N10 | Methylene chloride-methanol | 1-1 |

Basic systems:

| B1 | Methylene chloride-methanol-conc. $NH_3$ | 40-10-1 |
| B2 | Methylene chloride-methanol-conc. $NH_3$ | 50-10-1 |
| 3(sic) | Methylene chloride-methanol-conc. $NH_3$ | 60-10-1 |
| B4 | Methylene chloride-methanol-conc. $NH_3$ | 80-10-1 |
| B5 | Methylene chloride-methanol-conc. $NH_3$ | 100-10-1 |
| B6 | Ethyl acetate-ethanol-conc. $NH_3$ | 24-12-4 |
| B7 | Toluene-isopropanol-conc. $NH_3$ | 170-30-2 |

Acidic systems:

| A1 | Methylene chloride-methanol-water-acetic acid | 150-50-10-1 |
| A2 | Toluene-isopropanol-acetic acid | 170-30-2 |

EXAMPLE 1

N-Valeryl-N-[(2'-(1H-tetrazol-5-yl)biphenyl-4-yl)methyl]glycine 1.2 g of N-valeryl-N-[(2'-cyanobiphenyl-4-yl)methyl] glycine methyl ester and 2.18 g of tributyltin azide are heated to reflux in 40 ml of xylene for 24 hours. After this, the reaction mixture is concentrated and the residue is stirred in 1N NaOH at room temperature for 10 hours. The mixture is extracted with ether, and the aqueous phase is rendered acidic and extracted again with ether. This second ether phase is washed with brine, dried and concentrated. The crude product is chromatographed by means of flash chromatography (100 g of silica gel, eluent B1). Amorphous product, $R_f$: 0.29 (system $CH_2Cl_2$-methanol-conc. ammonia: 30-10-1).

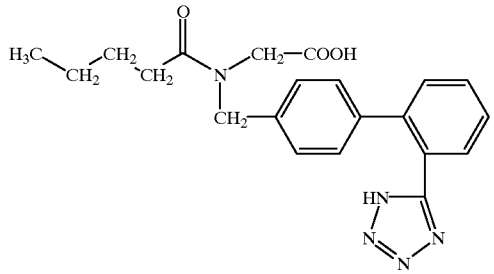

The starting material can be obtained, for example, as follows:

a) 2'-Cyanobiphenyl-4-carbaldehyde 250 g of 4-bromomethyl-2'-cyanobiphenyl (EP 253,310), 150 g of sodium acetate and 2.5 litres of glacial acetic acid are heated to reflux overnight and the mixture is then concentrated in a high vacuum. The residue is taken up in ethyl acetate, extracted with water, sodium bicarbonate and brine and the solvent is evaporated on a rotary evaporator. The crude product is dissolved in 3.1 litres of ethanol, treated with 430 ml of 2N NaOH and stirred overnight at room temperature. The reaction mixture is concentrated, taken up in ethyl acetate, washed with water and sodium carbonate and concentrated. The residue is suspended in hexane, filtered off with suction, washed and dried at 60° in a high vacuum for 20 hours. 4-Hydroxymethyl-2'-cyanobiphenyl is obtained as a white powder. $^1$H-NMR (DMSO): 4.58 ppm (d, 2 H), 5.3 ppm (t, 1 H), 7.6–8 ppm (aromatics, 8 H).

53 ml of oxalyl chloride in 2 litres of methylene chloride are cooled to −60°. A solution of 88 ml of dimethyl sulfoxide in 150 ml of methylene chloride is added dropwise at this temperature and the mixture is then stirred for 2 minutes. After this, 117 g of 4-hydroxymethyl-2'-cyanobiphenyl in 1 litre of methylene chloride are added dropwise at −60°. After addition has ended (about 5 minutes), the mixture is subsequently stirred for 15 minutes. After this, 390 ml of triethylamine are added dropwise. The mixture is then stirred at −60° for 2 minutes and allowed to warm to room temperature. The reaction mixture is poured into water, extracted with methylene chloride, and the organic phase is washed with dilute hydrochloric acid and brine, dried and concentrated. The product is stirred in hexane, filtered off with suction, washed and dried at 600 in a high vacuum. Elemental analysis: C 80.7%, H 4.5%, N 6.7%, O 7.7%.

b) N-[(2'-Cyanobiphenyl)-4-yl-methyl]glycine methyl ester 2.00 g of 2'-cyanobiphenyl-4-carbaldehyde, 1.22 g of glycine methyl ester hydrochloride and 9.6 g of molecular sieve 5A in 26 ml of tetrahydrofuran are stirred at room temperature for 36 hours and the mixture is then cooled to 0–5°. 680 mg of sodium cyanoborohydride (90%) dissolved in 4.8 ml of methyl alcohol are added, and the mixture is stirred at room temperature for 24 hours and then concentrated in vacuo. The crude product is separated by means of flash chromatography (180 g, ethyl acetate/petroleum ether: 1–1). $^1$H-NMR (DMSO): 3.63 ppm (s, 3 H), 3.79 ppm (s, 2 H), 7.4–8.0 ppm (aromatics, 10 H), 2.6 ppm (1 H).

c) N-Valeryl-N-[(2'-cyanobiphenyl-4-yl)methyl]glycine methyl ester 0.96 g of N-[(2'-cyanobiphenyl-4-yl)methyl]glycine methyl ester are dissolved in 9 ml of methylene chloride, and treated with 1.7 ml of triethylamine and then at 0° with 1.5 ml of N-valeryl chloride. The mixture is stirred at room temperature overnight and evaporated to dryness. The residue is taken up in ether and washed with sodium bicarbonate solution and brine. Flash chromatography (180 g, ethyl acetate/petroleum ether: 1—1) yields the product as a white powder. TLC (system N2) $R_f$: 0.68.

EXAMPLE 2

N-[(2'-(1H-Tetrazol-5-yl)biphenyl-4-yl)methyl]-N-valeryl-(L)-alanine

Starting from 1.24 g of N-valeryl-N-[(2'-cyanobiphenyl-4-yl)methyl]-(L)-alanine methyl ester and 2.73 g of tributyltin azide analogously to Example 1, the product is is (sic) obtained after flash chromatography (B3) and subsequent recrystallization from ethyl acetate as a white powder. M.p.: 115° (dec.).

The starting material can be obtained, for example, as follows:

N-[(2'-cyanobiphenyl-4-yl)methyl]-(L)-alanine methyl ester starting from 2.0 g of 2'-cyanobiphenyl-4-carbaldehyde, 1.34 g of (L)-alanine methyl ester hydrochloride, 680 mg of sodium cyanoborohydride and 2.4 g of molecular sieve 5 A and subsequent flash chromatography using the system N3. (TLC: system N1) $R_f$: 0.59.

N-valeryl-N-[(2'-cyanobiphenyl-4-yl)methyl]-(L)-alanine methyl ester starting from 1.65 g of N-[(2'-cyanobiphenyl)-methyl]-(L)-alanine methyl ester, 2.7 ml of triethylamine and 2.35 ml of n-valeryl chloride and subsequent flash chromatography (N2). (TLC: system N2) $R_f$: 0.62.

EXAMPLE 3

N-Valeryl-N-[(2'-(1H-tetrazol-5-yl)biphenyl-4-yl)methyl]-(L)-alanine methyl ester 0.3 g of acid from Example 2 is dissolved in 5 ml of methyl alcohol, treated with 0.5 ml of hydrochloric acid in methyl alcohol and the mixture is stirred at room temperature for 24 hours. The reaction mixture is then concentrated, taken up in methylene chloride, the solution is extracted with water, and the organic phase is dried and concentrated on a rotary evaporator. The product is obtained after flash chromatography (B1). M.p. of the amorphous material: 57–59°.

EXAMPLE 4

N-Valeryl-N-[(2'-(1H-tetrazol-5-yl)biphenyl-4-yl)methyl]-(DL)-p-fluorophenylalanine Starting from 2.3 g of N-valeryl-N-[(2'-cyanobiphenyl-4-yl)methyl]-(DL)-p-fluorophenylalanine methyl ester and 3.25 g of tributyltin azide, the product is obtained after flash chromatography (B1) by lyophilisation from tert-butyl alcohol. FAB-MS: m/e=502 (M+H)⁺.

The starting material can be obtained, for example, as follows:

N-[(2'-cyanobiphenyl-4-yl)methyl]-(DL)-p-fluorophenylalanine methyl ester starting from 2.33 g of 2'-cyanobiphenyl-4-carbaldehyde, 2.63 g of (DL)-p-fluorophenylalanine methyl ester, 790 mg of sodium cyanoborohydride and 11.0 g of molecular sieve 5 A and subsequent flash chromatography using system N3. (TLC: system N2) $R_f$: 0.36.

N-valeryl-N-[(2'-cyanobiphenyl-4-yl)methyl]-(DL)-p-fluorophenylalanine methyl ester starting from 2.1 g of N-[(2'-cyanobiphenyl-4-yl)methyl]-(DL)-p-fluorophenylalaninemethyl ester, 1.0 ml of triethylamine and 0.85 ml of n-valeryl chloride and subsequent flash chromatography (N3). (TLC: system N2) $R_f$: 0.64.

EXAMPLE 5

N-Valeryl-N-[(2'-(1H-tetrazol-5-yl)biphenyl-4-yl)methyl]-(DL)-p-fluorophenylalanine methyl ester Starting from 1.29 g of N-valeryl-N-[(2'-(1H-tetrazol-5-yl)biphenyl-4-yl)methyl]-(DL)-p-fluorophenylalanine according to Example 4, analogously to Example 3. FAB-MS: m/e=516 (M+H)⁺.

EXAMPLE 6

N-[3-(p-Fluorophenyl)-1-hydroxy-2-propyl]-N-[(2'-(1H-tetrazol-5-yl)biphenyl-4-yl)methyl]valeramide 0.5 g of N-valeryl-N-[(2'-(1H-tetrazol-5-yl)biphenyl-4-yl)methyl]-(DL)-p-fluorophenylalanine methyl ester from Example 5 in 5 ml of tetrahydrofuran at −70° is treated with 1.9 ml of diisobutylaluminium hydride. After 20 minutes, 0.2 ml of methyl alcohol is added and the mixture is allowed to warm to room temperature. The reaction mixture is treated with ether and water, and the organic phase is separated off, washed with brine, dried and concentrated. Flash chromatography (B2) yields the corresponding aldehyde. This is treated in 5 ml of ethyl alcohol at 0° with 27 mg of sodium borohydride and stirred at this temperature for 3.5 hours. After filtering and concentrating, the product is obtained by flash chromatography (N8) and lyophilisation from tert-butyl alcohol. FAB-MS: m/e=488 (M+H)⁺.

EXAMPLE 7

N-Valeryl-N-[(2'-carboxybiphenyl-4-yl)methyl]-(DL)-p-fluorophenylalanine

. . . (sic) N-Valeryl-N-[(2'-carboxybiphenyl-4-yl)methyl]-(DL)-p-flu or ophenylalanine methyl ester in 10 ml of methyl alcohol and 3 ml of water is treated with 0.45 ml of 2N NaOH. The mixture is stirred overnight at room temperature and then neutralized with 0.45 ml of 2N hydrochloric acid. The amorphous product is obtained after flash chromatography (B1) and lyophilisation from tert-butanol. FAB-MS: m/e=478 (M+H)⁺.PP

EXAMPLE 8

N-Valeryl-N-[(2'-carboxybiphenyl-4-yl)methyl]-(DL)-p-fluorophenylalanine methyl ester 840 mg of N-valeryl-N-[(2'-(trimethylsilylethoxycarbonyl)biphenyl-4-yl)methyl]-(DL)-p-fluorophenylalanine methyl ester in 10 ml of dimethylformamide are treated with 15.6 ml of a 0.5M solution of tetrabutylammonium fluoride in tetrahydrofuran, and the mixture is stirred overnight at room temperature. The reaction mixture is concentrated, the residue is taken. up in ethyl acetate, and the solution is washed with water and brine, dried and concentrated. The product is obtained after flash chromatography (B4) and lyophilisation from tert-butanol. FAB-MS: m/e=492 (M+H)⁺.

The starting material can be obtained, for example, as follows:

14.2 g of 4-methyl-2'-carboxybiphenyl (EP 253,310) are dissolved in 60 ml of acetonitrile and 10.7 ml of pyridine and 11.4 ml of trimethylsilylethanol are added. The mixture is treated at 0° with 15.1 g of dicyclohexylcarbodiimide and stirred at this temperature for 3 hours. After this, the reaction mixture is evaporated in a high vacuum, the residue is treated with ether, and dicyclohexylurea is filtered off. After flash chromatography (ethyl acetate/hexane 95:5), 4-methyl-2'-(trimethylsilylethoxycarbonyl)biphenyl (sic) is obtained as a slightly yellowish oil. (TLC: ethyl acetate/hexane 95:5) $R_f$: 0.42.

312 mg of 4-methyl-2'-(trimethylsilylethoxycarbonyl) biphenyl, 178 mg of N-bromosuccinimide, 5 mg of azoisobutyronitrile and 15 ml of carbon tetrachloride are heated to reflux for one hour. After cooling, the mixture is evaporated. Flash chromatography (ethyl acetate/hexane 95:5) yields 4-bromomethyl-2'-(trimethylsilylethoxycarbonyl)biphenyl as a slightly yellowish oil. $^1$H-NMR (CFCl$_3$): 0 ppm (s, 9 H), 0.7 ppm (t, 2 H), 4.5 ppm (s, 2 H), 7.1–8 ppm aromatics.

2.8 g of 4-bromomethyl-2'-(trimethylsilylethoxycarbonyl)biphenyl and 1.17 g of anhydrous sodium acetate are stirred overnight at 65° in glacial acetic acid and then boiled under reflux for 3 hours. The reaction mixture is evaporated, the residue is taken up in ethyl acetate and washed with water and sodium hydrogencarbonate, and the organic phase is dried and concentrated. The residue is introduced into 25 ml of ethanol, 6.3 ml of 1N NaOH are added and the mixture is stirred at room temperature for 30 minutes. It is evaporated in vacuo, and the residue is treated with ethyl acetate, washed with water and brine, dried and evaporated. Flash chromatography (N4) yields 4-hydroxymethyl-2'-(trimethylsilylethoxycarbonyl)biphenyl as a colourless oil. $^1$H-NMR (DMSO): 0 ppm (s, 9 H), 0.75 ppm (t, 2 H), 4.1 ppm (t, 2 H), 4.73 ppm (d, 2 H), 5.27 ppm (t, 1H), 7.2–7.7 ppm aromatics.

2'-(Trimethylsilylethoxycarbonyl)biphenyl-4-carbaldehyde is obtained analogously to Example 1a) starting from 6.5 g of 4-hydroxymethyl-2'-(trimethylsilylethoxycarbonyl)biphenyl, 1.87 ml of oxalyl chloride, 3.1 ml of dimethyl sulfoxide and 13.8 ml of triethylamine and subsequent flash chromatography using methylene chloride. $^1$H-NMR (CDCl$_3$): 0 ppm (s, 9 H), 0.8 ppm (t, 2 H), 4.2 ppm (t, 2 H), 7.2–8.1 ppm aromatics, 10.1 ppm (s, 1 H).

From (sic) starting from 1.0 g of 2'-(trimethylsilylethoxycarbonyl)biphenyl-4-carbaldehyde, 3.0 g of molecular sieve 5 A, 0.715 g of (D,L)-p-fluorophenylalanine methyl ester hydrochloride and 215 mg of sodium cyanoborohydride and subsequent flash chromatography (N3), N-[(2'-(trimethylsilylethoxy-carbonyl)biphenyl-4-yl)methyl](D,L)-p-fluorophenylalanine methyl ester is obtained analogously to Example 1b). (TLC: N3) $R_f$: 0.64.

Starting from 0.8 g of N-[(2'-(trimethylsilylethoxycarbonyl)biphenyl-4-yl)methyl](D,L)-p-fluorophenylalanine methyl ester, 0.29 ml of triethylamine and 0.25 ml of valeryl chloride, N-valeryl-N-[(2'-(trimethylsilylethoxycarbonyl)biphenyl-4-yl)methyl](D,L)-p-fluorophenylalanine methyl ester is obtained analogously to Example 1c) after flash chromatography (N3). (TLC: N3) $R_f$ value=0.65.

EXAMPLE 9

N-[3-(p-Fluorophenyl)-1-hydroxy-2-propyl]-N-[(2'-carboxybiphenyl-4-yl)-methyl]valeramide 290 mg of N-[3-(p-fluorophenyl)-1-hydroxy-2-propyl]-N-[2'-(trimethylsilylethoxycarbonyl)-4-yl-methyl] valeramide in 3 ml of dimethylformamide are treated at room temperature for 20 hours with 5.82 ml of a 0.5 molar solution of tetrabutylammonium fluoride in tetrahydrofuran. The mixture is concentrated in vacuo, and the residue is taken up in ethyl acetate, washed with water and brine and concentrated. After flash chromatography (N7) and lyophilisation, the product is obtained as a white powder. FAB-MS: m/e=446 (M+H)$^{30}$.

The starting material can be obtained, for example, as follows:

Starting from 1.5 g of 2'-(trimethylsilylethoxycarbonyl) biphenyl-4-carbaldehyde, 4.5 g of molecular sieve 5 A, 0.694 g of (D,L)-3-phenyl-2-aminopropan-1-ol and 321 mg of sodium cyanoborohydride, N-[(2'-(trimethylsilylethoxycarbonyl)biphenyl-4-yl)methyl]3-(p-fluorophenyl)-2-aminopropan-1-ol is obtained analogously to Example 1b) after flash chromatography (B5). $^1$H-NMR (DMSO): 0 ppm (2 s , 9 H), 0.73 ppm (2 t, 2 H), 2 ppm (b, 1 H), 2.73 ppm (m, 3 H), 3.3 ppm (m, 2 H), 3.83 ppm (s, 2 H), 4.1 ppm (2 t, 2 H), 4.6 ppm (t, 1 H), 7.15–7.8 ppm aromatics (8 H).

Starting from 365 mg of N-[(2'-(trimethylsilylethoxycarbonyl)biphenyl-4-yl)methyl]-3-(p-fluorophenyl)-2-aminopropan-1-ol, 0.136 ml of triethylamine, 0.112 ml of valeryl chloride and subsequent flash chromatography (N3), N-[3-(p-fluorophenyl)-1-hydroxy-2-propyl]-N-[(2'-(trimethylsilylethoxycarbonyl)-4-yl-methyl]valeramide is obtained analogously to Example 1c). FAB-MS: m/e=546 (M+H)$^{30}$.

EXAMPLE 10

N-[3-(Imidazol-4-yl)-1-hydroxy-2-(S)-propyl]-N-[(2'-carboxybiphenyl-4-yl)-methyl]valeramide Starting from 272 mg of N-[3-(imidazol-4-yl)-1-hydroxy-2-propyl]-N-[(2'-(trimethylsilylethoxycarbonyl)biphenyl-4-yl)methyl]valeramide and 5.54 ml of tetrabutylammonium fluoride solution, the product is obtained analogously to Example 9 and (sic) flash chromatography (B1). FAB-MS (M+H)$^{30}$ =436.

The starting material can be obtained, for example, analogously to Example 9 as follows:

Reaction of 1.5 g of 2'-(trimethylsilylethoxycarbonyl) biphenyl-4-carbaldehyde, 0.984 g of 3- (imidazol-4-yl)-2-(S)-aminopropan-1-ol-dihydrochloride, 321 mg of sodium cyanoborohydride and 4.5 g of molecular sieve 5 A yields N-[(2'-(trimethylsilylethoxycarbonyl)biphenyl-4-yl) methyl]-3-(imidazol-4-yl)-2-aminopropan-1-ol after flash chromatography (B5). (TLC) $R_f$ value (0.36).

Reaction of 0.45 g of N-[(2'-(trimethylsilylethoxycarbonyl)biphenyl-4-yl)methyl]-3-(imidazol-4-yl)-2-(S)-aminopropan-1-ol, 0.152 ml of triethylamine and 0.132 ml of valeryl chloride yields N-[3-(imidazol-4-yl)-1-hydroxy-2-propyl]-N-[(2'-(trimethylsilylethoxycarbonyl)biphenyl-4-yl)methyl] valeramide after flash chromatography (methylene chloride-methanol-conc. ammonia: 120-10-1). During working up, the aqueous phase is rendered slightly basic. FAB-MS: m/e=536 (M+H)$^+$.

EXAMPLE 11

N-Valeryl-N-[(2'-(1H-tetrazol-5-yl)biphenyl-4-yl) methyl]-(D)-alanine

Starting from 0.84 g of N-valeryl-N-[(2'-cyanobiphenyl-4-yl)methyl]-(D)-alanine methyl ester and 731 mg of tributyltin azide, the product is prepared analogously to Example 1 with subsequent flash chromatography (B1). FAB-MS: m/e=408 (M+H)⁺.

The starting material can be obtained, for example, analogously to Example 1b):

Reaction of 2.0 g of 2'-cyanobiphenyl-4-carbaldehyde, 9.6 g of molecular sieve 5 A, 1.34 g of (D)-alanine methyl ester hydrochloride and 680 mg of sodium cyanoborohydride yields N-[(2'-cyanobiphenyl-4-yl)methyl]-(D)-alanine methyl ester after flash chromatography (N3). ¹H-NMR (DMSO): 1.21 ppm (d, 3 H), 3.63 ppm (s, 3 H), 3.75 ppm (dd, 1 H), 4.56 ppm (d, 2 H), 4.58 ppm (d, 2 H), 5.31 ppm (t, 1 H), 7.4–8 ppm aromatics.

Reaction of 1.25 g of N-[(2'-cyanobiphenyl-4-yl)methyl]-(D)-alanine methyl ester, 2.1 ml of triethylamine and 1.8 ml of n-valeryl chloride analogously to Example 1c) yields N-valeryl-N-[(2'-cyanobiphenyl-4-yl)methyl]-(D)-alanine methyl ester after flash chromatography (N3) (TLC: N2) $R_f$: 0.61.

EXAMPLE 12

N-Valeryl-N-[(2'-(1H-tetrazol-5-yl)biphenyl-4-yl) methyl]-(L)-isoleucine

The product can be prepared starting from 2.0 g of N-valeryl-N-[(2'-cyanobiphenyl-4-yl)methyl]-(L)-isoleucine methyl ester and 3.19 g of tributyltin azide with subsequent flash chromatography (B1). FAB-MS (M+H)⁺= 450.

The starting material can be obtained, for example, analogously to Example 1 b):

The reaction of 2.0 g of 2'-cyanobiphenyl-4-carbaldehyde, 9.6 g of molecular sieve 5 A, 1.76 g of (L)-isoleucine methyl ester hydrochloride and 680 mg of sodium cyanoborohydride yields N-[(2'-cyanobiphenyl-4-yl)methyl]-(L)-isoleucine methyl ester after flash chromatography (ethyl acetate/hexane 1:3). ¹H-NMR (DMSO): 1.21 ppm (d, 3 H), 3.63 ppm (s, 3 H), 3.75 ppm (dd, 1 H), 4.56 ppm (d, 2 H), 4.58 ppm (d, 2 H), 5.31 ppm (t, 1 H), 7.4–8 ppm aromatics.

The reaction of 1.80 g of N-[(2'-cyanobiphenyl)-4-yl-methyl]-(L)-isoleucine methyl ester, 2.7 ml of triethylamine and 2.35 ml of n-valeryl chloride analogously to Example 1 c) yields N-valeryl-N-[(2'-cyanobiphenyl-4-yl)methyl]-(L)-isoleucine methyl ester after flash chromatography (N4). (TLC: N3) $R_f$: 0.43.

EXAMPLE 13

N-Valeryl-N-[(2'-(1H-tetrazol-5-yl)biphenyl-4-yl) methyl]-(L)-isoleucine methyl ester The product can be obtained analogously to Example 3 starting from 200 mg of N-valeryl-N-[(2'-(1H-tetrazol-5-yl)biphenyl-4-yl)methyl]-(L)-isoleucine with subsequent flash chromatography (B1). FAB-MS: m/e=464 (M+H)⁺.

EXAMPLE 14

N-Valeryl-N-[(2'-(1H-tetrazol-5-yl)biphenyl-4-yl)- methyl]-(L)-norvaline

The product can be prepared analogously to Example 1 starting from 0.30 g of N-valeryl-N-[(2'-cyanobiphenyl-4-yl)methyl]-(L)-norvaline methyl ester and 490 mg of tributyltin azide with subsequent flash chromatography (B1). FAB-MS (M+H)⁺=436.

The starting material can be obtained, for example, analogously to Example 1b):

The reaction of 2.0 g of 2'-cyanobiphenyl-4-carbaldehyde, 9.6 g of molecular sieve 5 A, 1.34 g of (L)-norvaline methyl ester hydrochloride and 680 mg of sodium cyanoborohydride yields N-[(2'-cyanobiphenyl-4-yl)methyl]-(L)-norvaline methyl ester after flash chromatography (N3). ¹H-NMR (DMSO): 0.83 ppm (t, 3 H), 1.33 ppm (m, 2 H), 1.55 ppm (m, 2 H), 3.62 ppm (s, 3 H), 3.1 ppm (m, 1 H), 7.3–8 ppm aromatics.

The reaction of 1.5 g of N-[(2'-cyanobiphenyl)-4-yl) methyl]-(L)-norvaline methyl ester, 2.35 ml of triethylamine and 2.15 ml of n-valeryl chloride analogously to Example 1 c) yields N-valeryl-N-[(2'-cyanobiphenyl-4-yl)methyl]-(L)-norvaline methyl ester after flash chromatography (ethyl acetate-hexane: 1–3) (TLC: B1) $R_f$: 0.9.

EXAMPLE 15

N-Valeryl-N-[(2'-(1H-tetrazol-5-yl)biphenyl-4-yl) methyll-(L)-isoleucine methyl ester The product can be obtained analogously to Example 3 starting from 200 mg of the compound according to Example 14 and subsequent flash chromatography (B1). FAB-MS: m/e=464 (M+H)⁺.

EXAMPLE 16

N-[(2'-(1H-Tetrazol-5-yl)biphenyl-4-yl)methyl]-N- valeryl-(L)-valine

The product can be prepared starting from 1.40 g of N-valeryl-N-[(2'-cyanobiphenyl-4-yl)-methyl](L)-valine methyl ester and 2.25 g of tributyltin azide with subsequent flash chromatography (B1). FAB-MS (M+H)⁺=436, melting interval 105–115° (from ethyl acetate).

The starting material can be obtained, for example, analogously to Example 1 b):

Reaction of 0.5 g of 2'-cyanobiphenyl-4-carbaldehyde, 2.5 g of molecular sieve 5 A, 0.815 g of (L)-valine methyl ester hydrochloride and 180 mg of sodium cyanoborohydride yields N-[(2'-cyanobiphenyl-4-yl)methyl]-(L)-valine methyl ester after flash chromatography (N3). (TLC: N3) $R_f$: 0.5.

Reaction of 1.15 g of N-[(2'-cyanobiphenyl-4-yl)methyl]-(L)-valine methyl ester, 0.625 ml of triethylamine and 0.56 ml of n-valeryl chloride analogously to Example 1c) yields N-valeryl-N-[(2'-cyanobiphenyl-4-yl)methyl]-(L)-valine methyl ester after flash chromatography (N3). (TLC: N2) $R_f$: 0.63.

EXAMPLE 17

N-Caproyl-N-[(2'-(1H-tetrazol-5-yl)biphenyl-4-yl) methyl]-(L)-alanine

The product can be prepared starting from 2.4 g of N-caproyl-N-[(2'-cyanobiphenyl-4-yl)methyl]-(L)-alanine methyl ester and 4.05 g of tributyltin azide with subsequent flash chromatography (B1). FAB-MS: m/e=422 (M+H)³⁰ .

The starting material can be obtained, for example, analogously to Example 2:

Reaction of 2.0 g of N-[(2'-cyanobiphenyl)-4-yl-methyl]-(L)-alanine methyl ester, 1.23 ml of triethylamine, and 1.22 ml of n-caproyl chloride yields N-caproyl-N-(2'-cyanobiphenyl-4-yl)methyl]-(L)-alanine methyl ester. (TLC: N2) $R_f$: 0.5.

EXAMPLE 18

N-Butyryl-N-[(2'-(1H-tetrazol-5-yl)biphenyl-4-yl)methyl]-(L)-alanine

The product can be prepared starting from 2.25 g of N-butyryl-N-[(2'-cyanobiphenyl-4-yl)methyl]-(L)-alanine methyl ester and 4.11 g of tributyltin azide with subsequent flash chromatography (B1). FAB-MS: m/e=394 (M+H)$^+$.

The starting material can be obtained, for example, analogously to Example 2:

Reaction of 2.0 g of N-[(2'-cyanobiphenyl-4-yl)methyl]-(L)-alanine methyl ester, 1.23 ml of triethylamine and 0.92 ml of n-butyryl chloride yields N-butyryl-N-[(2'-cyanobiphenyl-4-yl)methyl]-(L)-alanine methyl ester. (TLC: N2) $R_f$: 0.5.

EXAMPLE 19

N-Valeryl-N-[(2'-(1H-tetrazol-5-yl)biphenyl-4-yl)methyl]-(L)-2-aminobutyric acid The product can be prepared starting from 0.68 g of methyl N-valeryl-N-[(2'-cyanobiphenyl-4-yl)methyl]-(L)-2-aminobutyrate and 1.15 g of tributyltin azide. Crystallization from ether. M.p.: 102–104°. FAB-MS (M+H)$^+$=422.

The starting material can be obtained, for example, analogously to Example 1b):

Reaction of 3.0 g of 2'-cyanobiphenyl-4-carbaldehyde, 14.5 g of molecular sieve 5 A, 2.23 g of (L)-2-aminobutyric acid hydrochloride and 1075 mg of sodium cyanoborohydride yields methyl N-[(2'-cyanobiphenyl-4-yl)methyl]-(L)-2-aminobutyrate after flash chromatography (N3). $^1$H-NMR (DMSO): 0.88 ppm (t, 3 H), 1.62 ppm (m, 2 H), 2.53 ppm (b, 1 H), 3.15 ppm (m, 1 H), 3.63 ppm (s, 3 H), 3.62 ppm (d, 2 H), 3.81 ppm (d, 1 H).

Reaction of 0.54 g of methyl N-[(2'-cyanobiphenyl-4-yl)methyl]-(L)-2-aminobutyrate, 0.33 ml of triethylamine and 0.29 ml of N-valeryl chloride analogously to Example 1c) yields methyl N-valeryl-N-[(2'-cyanobiphenyl-4-yl)methyl]-(L)-2-aminobutyrate. (TLC: N2) $R_f$: 0.52.

EXAMPLE 20

N-Valeryl-N-[(2'-(1H-tetrazol-5-yl)biphenyl-4-yl)methvl]-(L)-cyclohexylalanine The product can be prepared starting from 4.0 g of N-valeryl-N-[(2'-cyanobiphenyl-4-yl)-methyl]-(L)-cyclohexylalanine methyl ester and 5.8 g of tributyltin azide and subsequent flash chromatography (B1). FAB-MS (M+H)$^+$=490.

The starting material can be obtained, for example, analogously to Example 1b):

Reaction of 9.35 g of 2'-cyanobiphenyl-4-carbaldehyde, 46 g of molecular sieve 5 A, 10.0 g of (L)-cyclohexylalanine methyl ester hydrochloride and 3.3 g of sodium cyanoborohydride yields N-[(2'-cyanobiphenyl-4-yl)methyl]-(L)-cyclohexylalanine methyl ester after flash chromatography (N3). (TLC: N3) $R_f$: 0.45.

Reaction of 9.0 g of N-[(2'-cyanobiphenyl-4-yl)methyl]-(L)-cyclohexylalanine methyl ester, 4.33 g of triethylamine and 3.75 ml of n-valeryl chloride analogously to Example 1c) yields N-valeryl-N-[(2'-cyanobiphenyl-4-yl)methyl]-(L)-cyclohexylalanine ester methyl ester after flash chromatography (N3). (TLC: N3) $R_f$: 0.55.

EXAMPLE 21

N-Valeryl-N-[(2'-(1H-tetrazol-5-yl)biphenyl-4-yl)methyl]-(L)-cyclohexvlalanine methyl ester The product can . . . (sic) obtained analogously to Example 3 starting from 1.02 g of the compound from Example 20. FAB-MS: m/e=504 (M+H)$^+$.

EXAMPLE 22

N-Valeryl-N-[(2'-(1H-tetrazol-5-yl)biphenyl-4-yl)methyl]-(D)-valine

The product can be prepared analogously to Example 11 starting from 3.8 g of N-valeryl-N-[(2-cyanobiphenyl-4-yl)methyl]-(D)-valine methyl ester and 6.17 g of tributyltin azide with subsequent flash chromatography (N8). FAB-MS (M+H)$^{30}$ =436.

The starting material can be obtained, for example, analogously to Example 1b):

Reaction of 4.0 g of 2'-cyanobiphenyl-4-carbaldehyde, 19.3 g of molecular sieve 5 A, 3.8 g of (D)-valine methyl ester hydrochloride and 1.43 g of sodium cyanoborohydride yields N-[(2'-cyanobiphenyl-4-yl)methyl]-(D)-valine methyl ester after flash chromatography (N3). (TLC: N2) $R_f$: 0.56.

Reaction of 3.2 g of N-[(2'-cyanobiphenyl)-4-yl-methyl]-(D)-valine methyl ester, 1.82 ml of triethylamine and 1.6 ml of N-valeryl chloride analogously to Example 1c) yields N-valeryl-N-[(2'-cyanobiphenyl-4-yl)methyl]-(D)-valine methyl ester after flash chromatography (N2). FAB-MS: m/e=407 (M+H)$^+$.

EXAMPLE 23

N-(2-Methoxvethyl)-N-[(2'-(1H-tetrazol-5-yl)biphenyl-4-yl)methyl]-n-valeramide A solution of 1.6 g (4.5 mmol) of crude N-[(2'-cyanobiphenyl-4-yl)methyl]-N-(2-methoxyethyl) valeramide and 1.8 g (5.5 mmol) of tri-n-butyltin azide in 15 ml of o-xylene is heated under reflux for 20–24 hours while passing a gentle stream of nitrogen through. After cooling, the solution is diluted with about 30 ml of toluene, treated with 15 ml of 1N aqueous sodium hydroxide solution and intensively stirred for 2 hours. The aqueous phase is separated off and rendered acidic with 16 ml of 1N aqueous hydrochloric acid. The precipitated products (sic) is isolated by extraction with ethyl acetate. The crude title compound is thus obtained as an oil which crystallizes from a little ethyl acetate, m.p. 120–122°.

The starting material can be prepared, for example, as follows:

a) 4-[N-(2-Methoxvethyl)aminomethyl]-2'-cyanobiphenyl

A solution of 5.45 g (20 mmol) of 4-bromomethyl-2'-cyanobiphenyl in 40 ml of 1,4-dioxane is treated with 7.5 g (100 mmol) of 2-methoxyethylamine and then heated to boiling under reflux for 8–10 hours. After thorough evaporation in a water jet vacuum, the evaporation residue is dissolved in 60 ml of 2N hydrochloric acid and extracted with 60 ml of ether. The hydrochloric acid solution is separated off and rendered alkaline with conc. sodium hydroxide solution. The precipitated oil is extracted with ether, and the ether solution is washed with water, dried over magnesium sulfate and evaporated. The crude title compound is thus obtained as an oil which is dissolved in a little ether and treated with a methanolic solution of hydrogen chloride gas. The crystalline hydrochloride thus obtained is recrystallized from 2-propanol and melts at 174–176°.

b) N-[(2'-cvanobiphenyl-4-yl)methyl]-N-(2-methoxyethyl)-n-valeramide 1.5 g (15 mmol) of N-valeryl chloride are added dropwise to a mixture of 3.7 g (12.2 mmol) of 4-[N-(2-methoxyethyl) aminomethyl]-2'-cyanobiphenyl hydrochloride and 3.1 g (31 mmol) of triethylamine in 50 ml of 1,4-dioxane while stirring and cooling with ice-water. The suspension is stirred at room temperature for 4–6 hours. After evaporating in a water jet vacuum, the reaction mixture is partitioned between 20 ml of water and 200 ml of ethyl acetate. The organic phase is washed successively with 10 ml each of 2N hydrochloric acid, saturated NaHCO$_3$ solution and brine, dried over magnesium sulfate and evaporated in vacuo. The tide compound thus obtained is obtained as an oil (R$_f$: 0.51 in system B7) and can be further reacted in crude form.

EXAMPLE 24

N-(2-Benzyloxvethyl)-N-[(2'-(1H-tetrazol-5-yl)biphenyl-4-yl)methyll-n-valeramide 6.5 g (15.2 mmol) of crude N-(2-benzyloxyethyl)-N-[(2'-cyanobiphenyl4-yl)methyl]-n-valeramide and 6.1 g of tri-n-butyltin azide are reacted and worked up analogously to Example 23. The crude title compound is thus obtained and, after recrystallization from a little ethyl acetate, melts at 109–110°.

The starting material can be prepared, for example, in the following manner:

a) 4-[N-(2-Benzyloxyethyl)aminomethyll-2'-cyanobiphenyl

The title compound is obtained from 2-benzyloxyethylamine (J. Am. Pharm. Assoc., Sci. Ed. 1952, 41, 257) analogously to Example 23 a) after flash chromatographic purification (silica gel; toluene-methanol 19:1) as a yellowish oil which has an R$_f$ value of 0.48 on TLC in system B7.

b) N-(2-Benzyloxyethyl)-N-[(2'-cyanobiphenyl-4-yl)methyl]-n-valeramide

The title compound is obtained from 4-[N-(2-benzyloxyethyl)aminomethyl]-2'-cyanobiphenyl analogously to Example 26 b). It has an R$_f$ value of 0.71 in TLC system B7 and can be further used in crude form.

EXAMPLE 25

N-(3-Methoxypropyl)-N-[(2'-(1H-tetrazol-5-yl)biphenyl-4-yl)methyl]-n-valeramide

The title compound is obtained analogously to Example 23 from 2.1 g (5.8 mmol) of crude N-[(2'-cyanobiphenyl-4-yl)methyl]-N-(3-methoxypropyl)-n-valeramide and 2.3 g (6.9 mmol) of tri-n-butyltin azide in 20 ml of o-xylene and with flash-chromatographic purification as a viscous oil having an R$_f$ of 0.33 in TLC system B6.

The starting material can be prepared, for example, in the following manner:

a) 4-[N-(3-Methoxypropyl)aminomethyl]-2'-cyanobiphenyl

The title compound is obtained from 3-methoxypropylamine analogously to Example 23 a) and forms a hydrochloride of m.p. 183–184° (from 2-propyl ether).

b) N-[(2'-Cyanobiphenyl-4-yl)methyl]-N-(3-methoxypropyl)-n-valeramide

The title compound is obtained from 25 a) analogously to Example 23 b). It has an R$_f$ of 0.55 in TLC system B7 and can be further reacted in crude form.

EXAMPLE 26

N-(3-Benzyloxypropyl)-N-[(2'-(1H-tetrazol-5-yl)biphenyl-4-yl)methyl]-n-valeramide 5.8 g (13 mmol) of compound 26 b) and 5.3 g (16 mM) (sic) of tri-n-butyltin azide are reacted and worked up analogously to Example 23. The crude title compound is thus obtained as an oil which is crystallized from a little 2-propanol ether and then melts at 112–1150.

The starting material can be prepared, for example, in the following manner:

a) 4-[N-(3-Benzyloxypropyl)aminomethyl]-2'-cyanobiphenyl

A solution of 6.0 g (22 mmol) of 4-bromomethyl-2'-cyanobiphenyl, 5.8 g (35 mmol) of 3-benzyloxypropylamine (Synthesis 1975, 590) and 3.6 g of triethylamine in 50 ml of 1,4-dioxane is heated to boiling under reflux for 18 hours. After working up analogously to Example 23 a), an oil is obtained which, after flash-chromatographic purification (ethanol:ethyl acetate: 1:4), gives the title compound (TLC system B7; R$_f$ value 0.39).

b) N-(3-Benzyloxypropyl)-N-[(2'-cyanobiphenyl-4-yl)methyl]-n-valeramide 2.0 g (16.7 mmol) of n-valeryl chloride are added dropwise while cooling with a water bath and stirring to a solution of 5.5 g (15.4 mmol) of compound 26 a) and 4.0 g of triethylamine in 40 ml of 1,4-dioxane. The reaction mixture is stirred at room temperature for 5–10 hours and worked up as in Example 23 b). The title compound is thus obtained as an oil (R$_f$ in system B7: 0.51) which is sufficiently pure for further reaction.

EXAMPLE 27

N-(2-Hvdroxyethyl)-N-[(2'-(1H-tetrazol-5-yl)biphenyl-4-yl)methyl]valeramide

A solution of 2.6 g (5.5 mmol) of the compound described in Example 24 in 90 ml of 1,4-dioxane is hydrogenated at room temperature with the addition of a total of 2.0 g of palladium-on-carbon catalyst (5%) until starting compound can no longer be detected (about 70 hours) in a TLC check (system B6). The catalyst is filtered off, the filtrate is evaporated in vacuo and the residue is dissolved in ethyl acetate. By washing the ethyl acetate solution with water, drying and evaporating in vacuo, a colourless foam is obtained whose $^1$H-NMR spectrum agrees with the structure of the title compound and which has an R$_f$ of 0.60 (TLC system B6).

EXAMPLE 28

N-(3-Hydroxypropyl)-N-[(2'-(1H-tetrazol-5-yl)biphenyl-4-yl)methyl]-n-valeramide 2.7 g (5.5 mmol) of the compound described in Example 26 are hydrogenated and worked up analogously to Example 27. A yellowish oil is obtained which, after flash-chromatographic purification (system S2), gives the title compound as a colourless foam which has an R$_f$ of 0.26 (system S2).

EXAMPLE 29

Methyl 2-amino-2-methyl-N-[(2'-(1H-tetrazol-5-yl)biphenyl-4-yl )methyl]-N-valerylpropanoate A solution of 9.4 g (24 mmol) of crude methyl 2-amino-N-[(2'-cyanobiphenyl-4-yl)methyl]-2-methyl-N-valerylpropanoate and 9.7 g (29 mmol) of tri-n-butyltin azide in 120 ml of o-xylene is heated to boiling under reflux for 30 hours and then worked up analogously to Example 23. The crude title compound thus obtained as an oil is flash-chromatographed using the system B6 for purification. The title compound thus obtained forms a foam and has an $R_f$ of 0.39 (system B6).

The starting product can be obtained, for example, in the following manner:

a) Methyl 2-amino-N-[(2'-cyanobiphenyl-4-yl)methyl]-2-methylpropanoate

A mixture of 10.9 g (40 mmol) of 4-bromomethyl-2'-cyanobiphenyl, 18.4 g (120 mmol) of methyl 2-amino-2-methylpropanoate hydrochloride (D. Leibfritz et al., Tetrahedron 1982, 38, 2165) and 22 g of potassium carbonate in 100 ml of dimethylformamide is heated with stirring in a bath at 800 for 18–20 hours. The suspension is filtered, the filtrate is evaporated in vacuo and the residue is partitioned between 200 ml of ethyl acetate and 50 ml of water. The organic phase is separated off, washed with 30 ml each of water and brine, dried and evaporated. The crude title compound is thus obtained. It forms a hydrochloride of m.p. 170–175° (from 2-propanol).

b) Methyl 2-amino-N-[(2'-cyanobiphenyl-4-yl)methyl]-2-methyl-N-valerylpropionate A solution of 7.4 g (24 mmol) of the compound 29 a) (as the base) and 3.7 g (29 mmol) of ethyldiisopropylamine in 100 ml of methylene chloride is treated dropwise with 3.5 g (29 mmol) of valeryl chloride with stirring. The reaction mixture is stirred at room temperature for 20–25 hours until starting amine can no longer be detected by TLC (system B7). Working-up analogously to Example 23 b) gives the crude title compound as a yellowish oil of $R_f$ 0.40 (system B7) which is further used in crude form.

EXAMPLE 30

N-[(2'-(1H-Tetrazol-5-yl)biphenyl-4-yl)methyl]-N-valeryl-3-aminopropanoic acid 393 mg of ethyl N-[(2'-cyanobiphenyl-4-yl)methyl]-N-valeryl-3-aminopropanoate are reacted analogously to Example 1. The crude product is purified on silica gel 60 (40–63 μm) using $CH_2Cl_2$—MeOH 95:5, $R_f$=0.15 (system N8).

The starting material can be prepared, for example, as follows:

a) Ethyl 3-[(2'-cyanobiphenyl-4-yl)methylamino]propanoate is obtained from 4.145 g of 2'-cyanobiphenyl-4-carbaldehyde and 3.135 g of ethyl 3-aminopropanoate hydrochloride analogously to Example 1 b) and purified on silica gel 60 (40–63 μm) using $CH_2Cl_2$—MeOH 95:5, $R_f$=0.21 (system N6).

b) Ethyl N-[(2'-cyanobiphenyl-4-yl)methyl]-N-valeryl-3-aminopropanoate is obtained from 1.542 g of ethyl 3-[(2'-cyanobiphenyl-4-yl)methylamino]propanoate analogously to Example 1 c), $R_f$=0.66 (system N6).

EXAMPLE 31 rac-N-[(2'-(1H-Tetrazol-5-yl)biphenyl-4-yl)methyl]-N-valeryl-3-amino-2-methyl-propanoic acid 785 mg of methyl rac-N-[(2'-cyanobiphenyl-4-yl)methyl]-N-valeryl-3-amino-2-methyl-propanoate are reacted analogously to Example 1 and purified by extraction, $R_f$=0.29 (system N8).

The starting material can be prepared, for example, as follows:

a) Methyl rac-3-amino-2-methylpropanoate hydrochloride is obtained from 10.312 g of rac-3-amino-2-methylpropanoic acid in 100 ml of methanol by dropwise addition of 7.3 ml of thionyl chloride, $R_f$=0.30 (system N8).

b) Methyl rac-3-[(2'-cyanobiphenyl-4-yl)methylamino]-2-methylpropanoate is obtained form 4.145 g of 2'-cyanobiphenyl-4-carbaldehyde and 3.072 g of methyl rac-3-amino-2-methylpropanoate hydrochloride analogously to Example 1 b) and purified on silica gel 60 (40–63 μm) using $CH_2Cl_2$—MeOH 97:3, $R_f$=0.31 (system N6).

c) Methyl rac-N-[(2'-cyanobiphenyl-4-yl)methyl]-N-valeryl-3-amino-2-methylpropanoate is obtained from 1.542 g of methyl rac-3-[(2'-cyanobiphenyl-4-yl)methylamino]-2-methyl-propanoate analogously to Example 1 c) and purified on silica gel 60 (40–63 μm) using $CH_2Cl_2$—MeOH 98:2, $R_f$=0.66 (system N6).

EXAMPLE 32

2-Amino-2-methyl-N-[(2'-(1H-tetrazol-5-yl)biphenyl-4-yl)methyl]-N-valerylpropanoic acid A solution of 2.6 g (6 mmol) of the ester described in Example 29 in 30 ml of methanol is treated with 35 ml of aqueous sodium hydroxide solution (20%) and heated to boiling under reflux and with stirring (about 35–40 hours) until the starting ester can no longer be detected by TLC (system B6). The solution is subjected to clarifying filtration, the methanol is evaporated in vacuo and the aqueous solution which remains is brought to pH 1–2 with conc. hydrochloric acid. The precipitated product is extracted with 200 ml of ethyl acetate, and the organic phase is separated off, washed with brine and dried over $MgSO_4$. The crude product isolated after evaporating the solvent is purified by flash chromatography by means of a mixture of 360 ml of methylene chloride, 40 ml of methanol, 4 ml of water and 2 ml of acetic acid. The homogeneous fractions containing only the product are combined and evaporated and give the title compound as a colourless foam which has an $R_f$ of 0.33 by TLC (system as mentioned above).

EXAMPLE 33

N-(5-Hydroxypentyl)-N-[(2'-(1H-tetrazol-5-yl)biphenyl-4-yl)methyl]-n-valeramide

A solution of 6.5 g (17 mmol) of crude N-[(2'-cyanobiphenyl-4-yl)methyl]-N-(5-hydroxypentyl)-n-valeramide and 6.8 g (20.4 mmol) of tri-n-butyltin azide in 70 ml of o-xylene is reacted and worked up analogously to Example 23. The crude product thus obtained is purified by flash chromatography (system B6). The fractions containing the product ($R_f$ 0.20) are evaporated. The free tetrazole is released by means of 1N hydrochloric acid from the ammonium salt of the title compound thus isolated and extracted with ethyl acetate. The title compound is thus obtained as a yellowish, glassy solid of $R_f$ 0.20 (system B6), which is obtained from ethyl acetate in crystalline form, m.p. 117–118°.

The starting material can be prepared, for example, in the following manner:

a) 4-[N-(5-Hydroxypentyl)-aminomethyl]-2'-cyanobiphenyl

A solution of 6.8 . . . (sic) (25 mmol) of 4-bromomethyl-2'-cyanobiphenyl and 12.9 g (125 mmol) of 5-amino-1-pentanol in 50 ml of 1,4-dioxane is heated to boiling under reflux for 2–3 hours. Working-up analogously to Example 23 a) using ethyl acetate as the solvent give (sic) the title compound as the hydrochloride of m.p. 189–190° (from 2-propanol).

b) N-[(2'-Cyanobiphenyl-4-yl)methyl]-N-(5-hydroxyipentyl)-n-valeramide

Using 9 ml of ethyldiisopropylamine and 50 ml of methylene chloride analogously to Example 26 b), the title compound is obtained from 5.1 g (17.3 mmol) of compound 33 a) and 2.3 g (19 mmol) of n-valeryl chloride as an oil of $R_f$ 0.36 (system B7), which is further reacted without further purification.

EXAMPLE 34 rac-N-[(2'-(1H-Tetrazol-5-yl)biphenyl-4-yl)methyl]-N-valeryl-3-aminobutanoic acid 3.390 g of ethyl rac-N-[(2'-cyanobiphenyl-4-yl)methyl]-N-valeryl-3-aminobutanoate are reacted analogously to Example 1 and purified by extraction, $R_f$=0.30 (system N8).

The starting material can be prepared, for example, as follows:

a) Ethyl rac-3-[(2'-cyanobiphenyl-4-yl)methylamino]butanoate is obtained from 4.145 g of 2'-cyanobiphenyl-4-carbaldehyde and 4.634 ml of ethyl rac-3-aminobutanoate analogously to Example 1 b) and purified on silica gel 60 (40–63 µm) using $CH_2Cl_2$—MeOH 98:2, $R_f$=0.25 (system N6).

b) Ethyl rac-N-[(2'-cyanobiphenyl-4-yl)methyl]-N-valeryl-3-aminobutanoate is obtained from 7.070 g of ethyl rac-3-[(2'-cyanobiphenyl-4-yl)methylamino]butanoate analogously to Example 1 c) and purified on silica gel 60 (40–63 µm) using $CH_2Cl_2$—MeOH 99:1, $R_f$=0.36 (system N6).

EXAMPLE 35

Ethyl rac-N-[(2'-(1H-tetrazol-5-yl)biphenyl-4-yl)methyl]-N-valeryl-2-(aminomethyl)-3-methylbutanoate 2.194 g of ethyl rac-N-[(2'-cyanobiphenyl-4-yl)methyl]-N-valeryl-2-(aminomethyl)-3-methylbutanoate are reacted analogously to Example 1 and purified on silica gel 60 (40–63 µm) using $CH_2Cl_2$—MeOH, $R_f$=0.48 (system N8).

The starting material can be prepared, for example, as follows:

a) Ethyl rac-2-[(2'-cyanobilphenyl-4-yl)methylaminomethyl]-3-methylbutanoate is obtained from 4.145 g of 2'-cyanobiphenyl-4-carbaldehyde and 3.180 g of ethyl rac-2-aminomethyl-3-methylbutanoate (Miyazaki et al. J. pharm. Soc. Jpn. 77, 415 (1957)) analogously to Example 1 b) and purified on silica gel 60 (40–63 µm) using $CH_2Cl_2$—MeOH 97:3, $R_f$=0.48 (system N6).

b) Ethyl rac-N-[(2'-cyanobiphenyl-4-yl)methyl]-N-valerml-2-(aminomethyl)-3-methylbutanoate is obtained from 2.519 g of ethyl rac-2-[(2'-cyanobiphenyl-4-yl)methylaminomethyl]-3-methylbutanoate analogously to Example 1 c) and purified on silica gel 60 (40–63 µm) using $CH_2Cl_2$—MeOH 99:1, $R_f$=0.67 (system N6).

EXAMPLE 36 rac-N-[(2'-(1H-Tetrazol4-yl)biphenyl-4-yl)methyl]-N-valeryl-2-(aminomethyl)-3-methylbutanoic acid 980 mg of ethyl rac-N-[(2'-(1H-tetrazol-5-yl)biphenyl-4-yl)methyl]-N-valeryl-2-(aminomethyl)-3-methylbutanoate in 3.1 ml of 2N NaOH are heated at 100° for 72 hours. Neutralization with 3.1 ml of 2N HCl and extraction with $CH_2Cl_2$ yields the product, $R_f$=0.30 (system N8).

EXAMPLE 37

N-Valeryl-N-[(2'-(1H-tetrazol-5-yl)biphenyl-4-yl)methyl]-(L)-valine 4.2 g of N-valeryl-N-[(2'-cyanobiphenyl-4-yl)methyl]-(L)-valine benzyl ester in 40 ml of xylene are heated to reflux with 5.7 g of tri-n-butyltin azide for 24 hours. After this, the mixture is evaporated to dryness. The crude product is then taken up in 40 ml of dioxane, treated with 400 mg of palladium-carbon (5%) and hydrogenated under normal pressure until it is saturated. The catalyst is filtered off, the solution is evaporated, the residue is taken up in ether and the product is extracted with 18 ml of 1N NaOH and 100 ml of water. The aqueous phase is washed with ether and, after acidifying with an excess of 1N hydrochloric acid, extracted with ethyl acetate. Recrystallization from diisopropyl ether yields the pure product of m.p. 116–117°.

The starting material can be prepared, for example, as follows:

a) N-(2'-Cyanobiphenyl-4-yl)methyl]-(L)-valine benzyl ester 4.38 g of 2'-cyanobiphenyl-4-carbaldehyde, 8.03 g of (L)-valine acid (sic) benzyl ester toluene sulfonic acid salt and 25 g of molecular sieve 5A in 80 ml of tetrahydrofuran are stirred at room temperature for 36 hours and then cooled to 0°. 2.19 g of sodium cyanoborohydride (90%), dissolved in 10 ml of methanol, are added, and the mixture is stirred at room temperature for 24 hours and then concentrated in vacuo. The reaction mixture is then filtered, the filtrate is concentrated, the residue is taken up in methylene chloride, and the solution is washed three times with water, dried and concentrated. The residue is taken up in water and treated with an excess of concentrated hydrochloric acid. The product is precipitated as the hydrochloride and filtered off. After recrystallization from ethyl acetate/hexane 1:1, the pure product of m.p. 153–155° is obtained.

b) N-Valeryl-N-[(2'-cyanobiphenyl-4-yl)methyl]-(L)-valine benzyl ester 5.5 g of N-[(2'-cyanobiphenyl-4-yl)methyl]-(L)-valine benzyl ester hydrochloride, 4.33 g of diisopropylethylamine and 3 ml of valeryl chloride are stirred at room temperature for 36 hours and the mixture is then evaporated to dryness. The residue is taken up in ether and washed with sodium bicarbonate and brine. The crude product is further processed without purification.

EXAMPLE 38

The following can be prepared in an analogous manner, for example according to one of Examples 23–26:

N-(3-phenoxypropyl)-N-(2'-(1H-tetrazol-5-yl)biphenyl-4-yl)methyl]valeramide,

N-(4-phenoxybutyl)-N-(2'-(1H-tetrazol-5-yl)biphenyl-4-yl)methyl]valeramide,

N-[2-(4-hydroxyphenyl)-ethyl]-N-(2'-(1H-tetrazol-5-yl)biphenyl-4-yl)methyl]valeramide, N-[3-(4-hydoxyphenyl)-propyl]-N-(2'-(1H-tetrazol-5-yl)biphenyl-4-yl)methyl]valeramide, N-(4-hydroxybutyl)-N-(2'-(1H-tetrazol-5-yl)biphenyl-4-yl)methyl]valeramide, N-(8-hydroxyoctyl)-N-(2'-(1H-tetrazol-5-yl)biphenyl-4-yl)methyl]valeramide, N-[2-(N-acetylamino)ethyl]-N-(2'-(1H-tetrazol-5-yl)biphenyl-4-yl)methyl]valeramide, N-[2-(N-methanesulfonylamino)ethyl]-N-(2'-(1H-tetrazol-5-yl)biphenyl-4-yl)-methyl]valeramide, N-[3-(N-acetylamino)propyl]-N-(2'-(1H-tetrazol-5-yl)biphenyl-4-yl)methyl]valeramide, methyl N-valeryl-N-(2'-(1H-tetrazol-5-yl)biphenyl-4-yl)methyl]-2-amino-2-phenyl-acetate;

for example analogously to one of Examples 9 and 10:

N-(3-hydroxy-1-methylpropyl)-N-(2'-(1H-tetrazol-5-yl)biphenyl-4-yl)methyl]valeramide, N-(2,2-dimethyl-3-hydroxypropyl)-N-(2'-(1H-tetrazol-5-yl)biphenyl-4-yl)-methyl]valeramide, N-(2-hydroxy-1-phenylethyl)-N-(2'-(1H-tetrazol-5-yl)biphenyl-4-yl)methyl]valeramide, N-[3-(N-(p-hydroxyphenylacetyl)amino)propyl]-N-(2'-(1H-tetrazol-5-yl)biphenyl-4-yl)-methyl]valeramide.

EXAMPLE 39

Ethyl 1-[N-[(2'-(1H-tetrazol-5-yl)biphenyl-4-yl)methyl]-N-valerylaminomethyl]-cyclopentane-1-carboxylate 3.75 g of ethyl N-[(2'-cyanobiphenyl-4-yl)methyl]-N-valeryl-1-aminomethylcyclopentane-1-carboxylate in 200 ml of xylene are treated with 10.4 g of tri-n-butyltin azide and heated to reflux for 41 h. The mixture is then evaporated in vacuo, and the tailback (sic) is taken up in 50 ml of 2N NaOH solution and extracted 3 times with ether. The aqueous phase is then acidified with 30 ml of 4N hydrochloric acid and extracted with dichloromethane. The product is obtained as a colourless foam by evaporating the organic phase, which was previously dried over $Na_2SO_4$, $R_f$=0.53 (system N8). MS (FAB): m/e 490 ($M^+$+H).

The starting material can be prepared, for example, as follows:

a) Ethyl 1-aminomethyl-cyclopentane-1-carboxylate is obtained by hydrogenating 33 g of ethyl 1-cyanocyclopentane-1-carboxylate (Alfred Bader Chemicals) in the presence of 10 g of Raney nickel, at 45° C. and under normal pressure in 330 ml of ethanol which contains about 4% ammonia. After filtering off the catalyst and removing the solvent in vacuo, the product is obtained by distillation, b.p. 71–74° C. at 0.75 mbar.

b) Ethyl N-[(2'-cyanobiphenyl-4-yl)methyl]-1-aminomethylcyclopentane-1-carboxylate is obtained from 4.15 g of 2'-cyanobiphenyl-4-carbaldehyde and 4.15 g of ethyl 1-aminomethylcyclopentane-1-carboxylate analogously to Example 1 b) and purified on silica gel 60 (40–63 μm) using $CH_2Cl_2$—MeOH 99.5:0.5, $R_f$=0.38 (system N6).

c) Ethyl N-[(2'-cyanobiphenyl-4-yl)-methyl]-N-valeryl-1-aminomethylcyclopentane-1-carboxylate is obtained from 4.70 g of ethyl N-[(2'-cyanobiphenyl-4-yl)-methyl]-1-aminomethylcyclopentane-1-carboxylate analogously to Example 1 c) and purified on silica gel 60 (40–63 μm) using $CH_2Cl_2$—MeOH 99.5:0.5, $R_f$=0.69 (system N6).

EXAMPLE 40

1-[N-[(2'-(1H-Tetrazol-5-yl)biphenyl-4-yl)methyl]-N-valerylaminomethyl]cyclopentane-1-carboxylic acid 0.979 g of N-[(2'-(1H-tetrazol-5-yl)biphenyl-4-yl)methyl]-N-valeryl-1-amino-methylcyclopentane-1-carboxylate are dissolved in 10 ml of ethanol and treated with 4 ml of 2N NaOH solution, and the mixture is heated to reflux for 23 h. After cooling to room temperature and adding 4.5 ml of 2N hydrochloric acid, the mixture is evaporated and the product is isolated by chromatography on silica gel 60 (40–63 μm) using $CH_2Cl_2$—MeOH 95:5, $R_f$=0.35 (system N8). MS (FAB): m/e 462 ($M^+$+H).

EXAMPLE 41 rac-cis/trans-N-[(2'-(1H-Tetrazol-5-yl)biphenyl-4-yl) and methyl]-N-valeryl3-aminocyclo-hexane-1-carboxylic acid and ethyl rac-cis/trans-N-[(2'-(1H-tetrazol-5-yl)biphenyl-4-yl)-methyl]-N-valeryl-3-aminocyclohexane-1-carboxylate (sic)

0.661 g of ethyl cis/trans-N-[(2'-cyanobiphenyl-4-yl)methyl]-N-valeryl-3-aminocyclo-hexane-1-carboxylate are reacted analogously to Example 1 and the mixture is purified by extraction. The crude product is purified on silica gel 60 (40–63 μm) using $CH_2Cl_2$—MeOH 95:5, $R_f$=0.33 (system N8) for the acid and $R_f$=0.67 (system N8) for the ester. MS (FAB): m/e 462 ($M^+$+H), 484 ($M^+$+Na) and m/e 490 ($M^+$+H), 512 ($M^+$+Na).

The starting material can be prepared, for example, as follows:

a) Ethyl rac-cis/trans-3-[2'-cyanobiphenyl-4-yl)methylamino]cyclohexane-1-carboxylate is obtained from 2.711 g of 4-bromomethyl-2'-cyanobiphenyl and 2.055 g of ethyl 3-aminocyclohexane-1-carboxylate (V. Škarić et al. J. C. S. Perkin I 1976, 1199) in the presence of N-methylmorpholine with 10 minutes' heating at 160° C. The crude product is purified on silica gel 60 (40–63 μm) using $CH_2Cl_2$—MeOH 9:1, $R_f$=0.73 (system N8).

b) Ethyl rac-cis/trans-N-[(2'-cyanobiphenyl-4-yl)methyl]-N-valeryl-3-aminocyclohexane1-carboxylate is obtained from 0.766 g of ethyl rac-cis/trans-3-[(2'-cyanobiphenyl-4-yl)-methylamino]cyclohexane-1-carboxylate analogously to Example 1 c) and purified on silica gel 60 (40–63 μm) using $CH_2Cl_2$—MeOH 99.5:0.5, $R_f$=0.56 (system N6).

EXAMPLE 42 cis-4-[N-[(2'-(1H-Tetrazol-5-l)biphenyl-4-yl)methyl]-N-valerylamino]cyclohexane-1-carboxylic acid 2.700 g of ethyl cis-N-[(2'-cyanobiphenyl-4-yl)methyl]-N-valeryl-4-amino-cyclohexane-1-carboxylate are reacted analogously to Example 1 and purified by extraction. $R_f$ 0.40 (system N8). MS (FAB): m/e 462 ($M^+$+H).

The starting material can be prepared, for example, as follows:

a) Ethyl cis-4-[(2'-cyanobiphenyl-4-yl)methylamino]cyclohexane-1-carboxyate is obtained from 4.145 g of 2'-cyanobiphenyl-4-carbaldehyde and 5.137 g of ethyl 4-aminocyclohexane-1-carboxylate (V. Škarić et al. J. Chem. Soc. Perkin 1 1976, 1199) anaogously to Exampe 1 b) and purified on silica gel 60 (40–63 μm) using $SCH_2C_2$—MeOH 99.5:0.5, $R_f$=0.18 (system N6).

b) Ethyl cis-N-[(2'-cyanobiphenyl-4-yl)methyl-N-valeryl-4-aminocyclohexane-1-carboxylate is obtained from 2.540 g of ethyl cis-4-[(2'-cyanobiphenyl4-yl)methylamino]cyclohexane-1-carboxylate analogously to Example 1 c) and purified on silica gel 60 (40–63 μm) using $CH_2Cl_2$—MeOH 98:2, $R_f$=0.32 (system N6).

EXAMPLE 43

Ethyl rac-cis-N-[(2'-(1H-tetrazol-5-yl)biphenyl-4-yl)methyl]-N-valeryl-2-amino-cyclohexane-1-carboxylate 1.350 g of ethyl rac-cis-N-[(2'-cyanobiphenyl-4-yl)methyl]-N-valeryl-2-amino-cyclohexane-1-carboxylate are reacted analogously to Example 1. The crude product is purified on silica gel 60 (40–63 μm) using $CH_2Cl_2$—MeOH 95:5, $R_f$=0.53 (system N8). MS (FAB): m/e 490 ($M^+$+H).

The starting material can be prepared, for example, as follows:

a) Ethyl rac-cis-2-[(2'-cyanobiphenyl-4-yl)methylamino]cyclohexane-1-carboxylate is obtained from 4.145 g of 2'-cyanobiphenyl-4-carbaldehyde and 5.137 g of ethyl rac-cis-2-aminocyclohexane-1-carboxylate (G. Toth et al. Justus Liebigs Ann. Chem. 1977, 529) analogously to Example 1 b)

and purified on silica gel 60 (40–63 μm) using CH₂Cl₂—MeOH 99:01, R$_f$=0.24 (system N6).

b) Ethyl rac-cis-N-[(2'-cyanobiphenyl-4-yl)methyl]-N-valeryl-2-amino-cyclohexane-1-carboxylate is obtained from 2.110 g of ethyl rac-cis-2-[(2'-cyanobiphenyl-4-yl)methylamino]cyclohexane-1-carboxylate and purified on silica gel 60 (40–63 μm) using CH₂Cl₂—MeOH 98:2, R$_f$=0.35 (system N6).

EXAMPLE 44 rac-cis-N-[(2'-(1H-Tetrazol-5-yl)biphenyl-4-yl)methyl]valeryl-2-aminocyclohexane-1-carboxylic acid 649 mg of ethyl rac-cis-N-[(2'-(1H-tetrazol-5-yl)biphenyl4-yl)methyl]-N-valeryl-2-aminocyclohexane-1-carboxylate are heated at 80° for 18 hours together with 10 ml of ethanol and 2 ml of 2N NaOH. The mixture is neutralized with 2 ml of 2N HCl and evaporated. The crude product is purified on silica gel 60 (40–63 μm) using CH₂Cl₂—MeOH (95:5), R$_f$=0.30 (system N8). MS (FAB): m/e 462 (M⁺+H), 484 (M⁺+Na).

EXAMPLE 45

Ethyl 2-ethyl-2-[N-[(2'-(1H-tetrazol-5-yl)biphenyl-4-yl)methyl]-N-valerylaminomethyl]-butyrate 3.28 g of ethyl N-[(2'-cyanobiphenyl-4-yl)methyl]-N-valeryl-2-aminomethyl-2-ethylbutyrate are reacted analogously to Example 1 and purified by extraction. R$_f$=0.52 (system N8). MS (FAB): m/e 492 (M⁺+H), 514 (M⁺+Na).

The starting material can be prepared, for example, as follows:

a) Ethyl 2-aminomethyl-2-ethylbutyrate is obtained by hydrogenating 12.83 g of ethyl 2-ethyl-2-cyanobutyrate (Pfaltz & Bauer Inc.) in the presence of 4 g of Raney nickel, at 44° C. and under normal pressure in 130 ml of ethanol which contains 4% ammonia. After separating off the catalyst the mixture is evaporated in vacuo and the liquid remaining is distilled in vacuo. B.p. 60–61° C. at 0.70 mbar.

b) Ethyl N-[(2'-cyanobiphenyl-4-yl)methyl]-2-aminomethyl-2-ethylbutfrate is obtained from 2.711 g of 4-bromomethyl-2'-cyanobiphenyl and 4.332 g of ethyl 2-aminomethyl-2-ethylbutyrate analogously to Example 41 a) and purified on silica gel 60 (40–63 μm) using CH₂Cl₂—MeOH 97:3, R$_f$=0.54 (system N6).

c) Ethyl N-[(2'-cyanobiphenyl-4-yl)methyl]-N-valeryl-2-aminomethyl-2-ethylbutyrate is obtained from 3.256 g of ethyl N-[(2'-cyanobiphenyl-4-yl)methyl]-2-aminomethyl-2-ethylbutyrate analogously to Example 1 c) and purified on silica gel 60 (40–63 μm) using CH₂Cl₂—MeOH 99:1, R$_f$=0.67 (system N6).

EXAMPLE 46

Ethyl N-[(2'-(1H-tetrazol-5-yl)biphenyl-4-yl)methyl]-N-valeryl-3-amino-2,2-dimethylpropionate.

4.21 g of ethyl N-[(2'-cyanobiphenyl-4-yl)methyl]-N-valeryl-3-amino-2,2-dimethylpropionate are reacted analogously to Example 1. The crude product is purified on silica gel 60 (40–63 μm) using CH₂Cl₂—MeOH 9:1, R$_f$=0.60 (system N8). MS (FAB): m/e 464 (M⁺+H), 486 (M⁺+Na).

The starting material can be prepared, for example, as follows:

a) Ethyl N-[(2'-cyanobiphenyl-4-yl)methyl]-3-amino-2,2-dimethylpropionate is obtained from 2.711 g of 4-bromomethyl-2'-cyanobiphenyl and 3.630 g of ethyl 3-amino-2,2'-dimethylpropionate (Buckley et al. J. Chem. Soc. 1947, 1503) analogously to Example 41 a) and further used as the crude product, R$_f$=0.54 (system N6).

b) Ethyl N-[(2'-cyanobiphenyl-4-yl)methyl]-N-valeryl-3-amino-2,2-dimethylpropionate is obtained from 3.36 g of ethyl N-[(2'-cyanobiphenyl-4-yl)methyl]-3-amino-2,2-dimethylpropionate analogously to Example 1 c) and purified by extraction, R$_f$=0.63 (system N6).

EXAMPLE 47

1-[N-[(2'-(1H-Tetrazol-5-yl)biphenyl-4-yl)methyl]-N-valerylaminomethyl]cyclopentane-1-[N'-[2-(4-hydroxyphenyl)ethyl]]carboxamide 0.507 g of N-[(2'-(1H-tetrazol-5-yl)biphenyl-4-yl)methyl]-N-valeryl-1-aminomethyl-cyclopentane-1-carboxylic acid is dissolved in 4 ml of DMF and treated with 0.210 g of tyramine hydrochloride, 0.225 ml of Hünig base and 0.164 g of HOBT. The mixture is cooled to 0° C. and 0.274 g of EDCl is added. After stirring at room temperature for 48 hours, the mixture is evaporated in vacuo, the residue is taken up in 75 ml of ethyl acetate and the solution is washed with 25 ml of 1N hydrochloric acid. The organic phase is dried over Na₂SO₄ and freed of solvent in vacuo. The crude product thus obtained is purified on silica gel 60 (40–63 μm) using CH₂Cl₂—MeOH 95:5, R$_f$=0.43 (system N8). MS (FAB): m/e 581 (M⁺+H), 603 (M⁺+Na).

EXAMPLE 48

N-Valeryl-N-[(2'-(1H-tetrazol-5-yl)biphenyl-4-yl)methyl]-(L)-valine[N-p-hydroxynaphthyl]amide 0.5 g of the compound from Example 16, 0.21 g of tyramine hydrochloride, 0.225 ml of N-ethyldiisopropylamine, 0.164 g of 1-hydroxybenzotriazole and 0.296 g of dicyclohexylcarbodiimide are stirred at room temperature in 4 ml of DMF for 48 h. After evaporating the solvent in vacuo, the residue is stirred in a mixture of 4 ml of CH₂Cl₂—MeOH—AcOH 94:3:3 for 1 h. After evaporating, the mixture is separated by means of flash chromatography (100 g, system N6). After lyophilizing from t-BuOH, the product is obtained as an amorphous powder. FAB-MS: m/e=555 (M+H)⁺.

EXAMPLE 49

N-Valeryl-N-[(2'-(1H-tetrazol-5-yl)biphenyl-4-yl)-methyl]-(L)-tet-leucine

Starting from 240 mg of N-valeroyl-N-[(2'-cyanobiphenyl-4-yl)methyl]-(L)-tert-leucine (sic) methyl ester and 399 mg of tributyltin azide, the product is obtained after flash chromatography (B2). M.p. 122–124 . . . (sic).

The starting material can be obtained, for example, as follows:

a) N-(2'-cyanobiphenyl-4-yl)methyl]-(L)-tert-leucine methyl ester starting from 2.5 g of 2'-cyanobiphenyl-4-carbaldehyde, 4.39 g of (L)-tert-leucine methyl ester hydrochloride, 895 mg of sodium cyanoborohydride (85%) and 12.5 g of molecular sieve 5A with subsequent flash chromatography using system N3. (TLC system N2) R$_f$: 0.58.

b) N-Valeryl-N-[(2'-cyanobiphenyl-4-yl)methyl]-(L)-tert-leucine methyl ester starting from 1.2 g of N-(2'-cyanobiphenyl-4-yl)methyl]-(L)-tert-leucine methyl ester, 0.65 ml of triethylamine and 0.565 ml of n-valeryl chloride with subsequent flash chromatography (N4). (TLC system N3) $R_f$: 0.56.

EXAMPLE 50

N-Valeryl-N-[(2'-(1H-tetrazol-5-yl)biphenyl-4-yl) methyl]-(L)-valine methyl ester 0.8 g of N-valeroyl-N-[(2'-(1H-tetrazol-5-yl)biphenyl-4-yl)methyl]-(L)-valine (sic) methyl ester is obtained analogously to Example 3 starting from 4.4 g of N-valeryl-N-[(2-(1H-tetrazol-5-yl)biphenyl-4-yl)methyl]-(L)-valine, which are esterified in MeOH/HCl. Flash chromatography (ethyl acetate/hexane 1:3). FAB-MS: m/e=450 (M+H)$^+$.

EXAMPLE 51

N-[(2'-(1H-Tetrazol-5-yl)biphenyl-4-yl)methyl]-N-valeryl-(L)-valinol 0.8 g of N-valeryl-N-[(2'-(1H-tetrazol-5-yl)biphenyl-4-yl)methyl]-(L)-valine methyl ester is dissolved in 30 ml of ThF, treated at 5° C. with 83 mg of lithium borohydride and stirred at room temperature for 24 h. The reaction mixture is then concentrated, treated with water and adjusted to pH 2 with hydrochloric acid, a white precipitate forming. The mixture is extracted with ethyl acetate, washed with water and brine, dried and finally separated by means of flash chromatography (CH$_2$Cl$_2$—MeOH 5:1). FAB-MS: m/e=422 (M+H)$^+$.

EXAMPLE 52

N-(4-Phenoxybutyl)-N-[(2'-(1H-tetrazol-5-yl) biphenyl-4-yl)methyl]-n-valeramide 3.3 g (7.5 mmol) of crude N-[(2'-cyanobiphenyl-4-yl)methyl]-N-(4-phenoxybutyl)-n-valeramide and 3.0 g (9 mmol) of tri-n-butyltin azide are reacted and worked up analogously to Example 23. The title compound is thus obtained, and additionally purified by flash chromatography (toluene-methanol 4:1), as a viscous oil, $R_f$ 0.50 (system B6).

The starting material can be prepared, for example, in the following manner:

a) 4-[N-(4-Phenoxybutyl)aminomethyl]-2'-cyanobiphenyl

The title compound, whose hydrochloride melts at 103–104° (from isopropanol-ethyl acetate), is obtained from 4-phenoxybutylamine analogously to Example 23 a).

b) N-[(2'-Cyanobiphenyl-4-yl)methyl]-N-(4-phenoxybutyl)-n-valeramide

The title compound is obtained from the compound described under a) analogously to Example 23 b) as a yellow oil of $R_f$ 0.71 (system B7) which is further used in crude form.

EXAMPLE 53 rac-N-[(2'-(1H-Tetrazol-5-yl)biphenyl-4-yl)methyl] phenylglycine 11.0 g (21 mmol) of N-[(2'-cyanobiphenyl-4-yl)methyl]-N-valeryl-phenylglycine benzyl ester are reacted with 8.5 g (25.5 mmol) of tri-n-butyltin azide in 60 ml of o-xylene analogously to Example 1 and then hydrolysed using 100 ml of 2N KOH for 3 hours. The crude title compound is obtained by acidifying the aqueous phase with 2N hydrochloric acid and extracting with toluene and is obtained in crystalline form from a little toluene. The crystals thus obtained of m.p. 145–148° contain ⅓ mol equivalent of toluene.

The starting material can be prepared, for example, as follows:

a) rac-N-[(2'-Cyanobiphenyl-4-yl)-methyl]phenylglycine benzyl ester 24.8 g (60 mmol) of rac. phenycglycine benzyl ester tosylate and 8.2 g (30 mmol) of 4-bromomethyl-2'-cyanobiphenyl are kept at 80° with stirring for 2 hours together with 15.5 g of diisopropylethylamine (Hünig base) in 60 ml of DMF. The reaction mixture is then poured into ice-water and extracted with ethyl acetate. The ethyl acetate is separated off and stirred with 2N hydrochloric acid. The hydrochloride of the tide compound which precipitates as an oil is separated off, converted into the base using sodium carbonate solution and further used in crude form ($R_f$ 0.65 in system B7).

b) N-[(2'-Cyanobiphenyl-4-yl)methyl]-N-valerylphenylplycine benzyl ester 9.4 g (21.7 mmol) of the crude compound described under a) is dissolved in 45 ml of methylene chloride together with 5.7 g (44 mmol) of Hmtnig base and treated with 3.14 g (26 mmol) of valeryl chloride. The solution is allowed to stand for 30–40 hours. Working-up analogously to Example 1 c give (sic) the crude title compound as a viscous oil of $R_f$ 0.73 (system B7) which is further used in crude form.

EXAMPLE 54

N-[(2'-(1H-Tetrazol-5-yl)biphenyl-4-yl)methyl]-N-valelyl-(L)-valine

A solution of 21.1 g (40 mmol) of N-[(2'-(1H-tetrazol-5-yl)biphenyl-4-yl)methyl]-N-valeryl-(L)-valine benzyl ester in 210 ml of methanol is hydrogenated at room temperature with the addition of 4 g of Pd/C (10%) until the calculated amount of hydrogen has been absorbed (24 hours). The crude acid is obtained by filtration and evaporation of the solution. It is partitioned between 80 ml of 2N potassium hydroxide solution and 50 ml of ether. The aqueous phase is separated off and rendered acidic, and the title compound is isolated by extraction with ethyl acetate. It is obtained from ethyl acetate in crystalline form and has a melting interval of 105–115° and an optical rotation $[\alpha]_D^{20}$ of −69.95°±0.05° (c=1% in methanol).

The starting material can be prepared, for example, as follows:

a) N-[(2'-Cyanobiphenyl-4-yl)methyl]-(L)-valine benzyl ester

A solution of 13.6 g (50 mmol) of 4-bromomethyl-2'-cyanobiphenyl, 22.8 g (60 mmol) of (L)-ValOBz tosylate and 34 ml of Hiunig base in 100 ml of DMF is stirred at 80° for 1 hour. The reaction mixture is then cooled, poured into 300 ml of ice-water and extracted with 150 ml of ethyl acetate. By washing the extract with aqueous potassium bicarbonate solution, drying and evaporating, the crude title compound is obtained as an oil which forms a hydrochloride of m.p. 172–173°.

b) N-[(2'-Cyanobiphenyl-4-yl)methyl]-N-valeryl-(L)-valine benzyl ester 6.2 g (15.5 mmol) of N-[(2'-cyanobiphenyl-4-yl)methyl]-(L)-valine benzyl ester and 8.0 ml of Huinig base, dissolved in 50 ml of methylene chloride, are treated with 2.3 ml of valeryl chloride with stirring and further processed analogously to Example 29b. The title compound is thus obtained as a yellow oil which is further used in crude form ($R_f$ 0.51, toluene-methanol 19:1)

c) N-[(2'-(1H-Tetrazol-5-yl)biphenyl-4-yl)methyl]-N-valeryl-(L)-valine benzyl ester 6.6 g (13.6 mmol) of crude N-[(2'-cyanobiphenyl-4-yl)methyl]-N-valeryl-(L)-valine benzyl ester and 6.0 g (18 mmol) of tributyltin azide in 75 ml of o-xylene are heated to boiling with stirring for 48 hours. After 24 hours, 2.0 g of tributyltin azide are added. Working-up analogously to Example 23 using 110 ml of 1N potassium hydroxide solution for 20 minutes gives the title compound as a yellowish oil which has an $R_f$ of 0.40 (system A2) and an optical rotation $[\alpha]_D^{20}$ of $-36.6°$ (c=1% in methanol).

EXAMPLE 55

N-[(2'-(1H-Tetrazol-5-yl)biphenyl-4-yl)methyl]-N-valeryl-(L)-valine benzyl ester A solution of 91 g (about 100 mmol) of crude N-[(2'-(1-triphenylmethyl-tetrazol-5-yl)biphenyl-4-yl)methyl]-N-valeryl-(L)-valine benzyl ester in 300 ml of dioxane is treated at 60° with 300 ml of 1N hydrochloric acid and kept at 60° for 2 hours. The dioxane is then evaporated in vacuo and the aqueous phase is rendered alkaline with 2N potassium hydroxide solution. Neutral portions are extracted with ether. The aqueous phase gives the crude title compound as an oil ($R_f$ 0.40 in system A2) by acidifying and extracting with ethyl acetate.

The starting material can be prepared, for example, as follows:

a) N-[(2'-(1-Triphenylmethyltetrazol-5-yl)biphenyl-4-yl)methyl]-(L)-valine benzyl ester The title compound ($R_f$ 0.78 in system B6) is obtained from 4-bromomethyl- 2'-(1-triphenylmethyltetrazol-5-yl)biphenyl analogously to Example 57a and is further used in crude form.

b) N-[(2'-(1-Triphenylmethyltetrazol-5-yl)biphenyl-4-yl)methyl]-N-valeryl-(L)-valine benzyl ester The compound mentioned under a) is reacted and worked up using 2.5 equivalents of valeryl chloride and 5 equivalents of Hunig base in methylene chloride analogously to Example 29b. The title compound thus obtained is further reacted in crude form.

EXAMPLE 56

2-Amino-N-butyryl-2-methyl-N-[(2'-(1H-tetrazol-5-yl)biphenyl-4-yl)methyl]propanoic acid A solution of 2.1 g (4.2 mmol) of benzyl 2-amino-N-butyryl-2-methyl-N-[(2'-(1H-tetrazol-5-yl)biphenyl-4-yl)methyl]propanoate in 20 ml of methanol is hydrogenated at an initial pressure of 5 bar with the addition of 0.2 g Pd/C (10%) until the starting benzyl ester can no longer be detected in the TLC (system B6, A2). The title compound of m.p. 187–189° is obtained by filtration, evaporation of the solvent and recrystallization of the residue from $CH_3CN$.

The starting material can be prepared, for example, as follows:

a) Benzyl 2-amino-N-[(2'-cyanobiphenyl-4-yl)-2-methylpropanoate

The title compound is obtained using benzyl 2-amino-2-methylpropanoate tosylate analogously to Example 29a and ... (sic) a hydrochloride of m.p. 200–202° (ethyl acetate-4N HCl in absolute ethanol).

b) Benzyl 2-amino-N-butyryl-N-[(2'-cyanobiphenyl-4-yl)-2-methylpropanoate

A solution of 6.3 g (15 mmol) of the hydrochloride of the compound described under a) and 10.2 ml (60 mmol) of Hunig base in 60 ml of methylene chloride is treated with 1.8 g (16 mmol) of butyryl chloride and the mixture is stirred overnight. The reaction is completed by further additions of acid chloride and Hinig base. Working-up analogously to Example 23b gives the title compound which is further reacted in crude form.

c) Benzyl 2-amino-N-butyryl-2-methyl-N-[(2'-(1H-tetrazol-5-yl)biphenyl-4-yl)methyl]propanoate The title compound of m.p. 203–204° (from ethyl acetate) is obtained from the compound (6 g, crude) described under b) and 5.2 g of tributyltin azide in 50 ml of o-xylene analogously to Example 23.

EXAMPLE 57

N-(4-Hydroxybutyl)-N-[(2'-(1H-tetrazol-5-yl)biphenyl-4-yl)methyl]-n-valeramide

The title compound of m.p. 110–111° (from ethyl acetate) is obtained from N-[(2'-cyanobiphenyl-4-yl)methyl]-N-(4-hydroxybutyl)-n-valeramide analogously to Example 33.

The starting material can be prepared, for example, as follows:

a) 4-[N-(4-Hydroxybutyl)aminomethyl]-2'-cyanobiphenyl

The title compound is obtained using 4-aminobutanol analogously to Example 33a) as an oil ($R_f$ 0.18 in system B7) which is further used in crude form.

b) N-[(2'-Cyanobiphenyl-4-yl)methyl]-N-(4-hydroxybutyl)-n-valeramide

The title compound is obtained from the compound described under a) analogously to Example 33b) as an oil ($R_f$ 0.37) which is further reacted in crude form.

EXAMPLE 58

N-[(3-Bromo-2'-(1H-tetrazol-5-yl)biphenyl-4-yl)methyl]-N-valeryl-(L)-valine benzyl ester A solution of 4.5 g (8 mmol) of N-[(3-bromo-2'-cyanobiphenyl-4-yl)methyl]-N-valeryl-(L)-valine benzyl ester and 3.4 g (10.4 mmol) of tributyltin azide in 50 ml of xylene is heated to boiling under reflux for 20 hours. Working-up analogously to Example 54 and "flash"-chromatographic purification (toluene-methanol 4:1) gives the title compound as a colourless foam ($R_f$ 0.57, system A2).

The starting material can be prepared, for example, as follows:

a) 3'-Bromo-4'-methyl-1.1'-biphenyl-2-carbonitrile

A suspension of 21.0 g (0.157 mol) of anhydrous aluminium chloride in 800 ml of tetrachloroethane is treated with 25.0 g (0.129 mol) of 4'-methyl-1,1'-biphenyl-2-carbonitrile and brought to an internal temperature of 60° with stirring. As soon as the aluminium chloride has gone into solution, a solution of 20.7 g (0.129 mol) of bromine in 100 ml of tetrachloroethane is added dropwise at an internal temperature of 60°. The reaction mixture is stirred at 60° for 24 hours. After addition of a further 6.2 g of aluminium chloride and warming to 60–70°, starting material can no longer be detected in the TLC (toluene). The reaction mixture is then decomposed with 20 ml of conc. hydrochloric acid with ice-cooling, and the organic phase is separated off and evaporated in vacuo. The dark residue is dissolved in ethyl acetate, washed with water and sodium carbonate solution, dried ($MgSO_4$) and evaporated. The crude product is purified by flash chromatography, as a result of which 22.0 g (62% of theory) of the title compound are obtained, m.p. 104–106° (from cyclohexane).

b) 3'-Bromo-4'-bromomethyl-1,1'-biphenyl-2-carbonitrile 5.6 g (0.035 mol) of bromine, dissolved in 20 ml of tetrachloroethane, are added dropwise at 100–110° with UV irradiation to a solution of 8.9 g (0.033 mol) of 3'-bromo-4'-methyl-1,1'-biphenyl-2-carbonitrile in 900 ml of tetrachloroethane after addition of 0.1 g of benzoyl peroxide. After 30 minutes, the reaction mixture is cooled and evaporated in vacuo. The crystalline residue is recrystallized from ethyl acetate and gives 4.1 g of the title compound of m.p. 152–153°.

c) N-[(3-Bromo-2'-cyanobiphenyl-4-yl)methyl]-(L)-valine benzyl ester

A solution of 4.63 g (12.2 mmol) of (L)-valine benzyl ester tosylate and 4.8 ml of Hünig base in 20 ml of DMF is treated with a solution of 3.3 g (9.4 mmol) of the compound described under b) and the mixture is stirred at 100° for 4 hours. Working-up analogously to Example 54a and "flash"-chromatographic purification (n-hexane-ethyl acetate 4:1) lead to the title compound as a reddish brown oil of $R_f$ 0.21 (n-hexane-ethyl acetate 4:1).

d) N-[(3-Bromo-2'-cyanobiphenyl-4-yl)methyl]-N-valeryl-(L)-valine benzyl ester

The title compound is obtained from the compound mentioned under c) analogously to Example 54b as a yellow oil of $R_f$ 0.17 (n-hexane-ethyl acetate).

EXAMPLE 59

N-[(3-Bromo-2'-(1H-tetrazol-5-yl)biphenyl-4-yl)methyl]-N-valeryl-(L)-valine

A solution of 2.4 g (4 mmol) of N-[(3-bromo-2'-(1H-tetrazol-5-yl)biphenyl-4-yl)methyl]-N-valeryl-(L)-valine benzyl ester in 90 ml of dioxane is hydrogenated at 5 bar and at room temperature with the addition of 1.2 g of Pd/C (10%) until the calculated amount of hydrogen has been absorbed. After evaporation of the filtered solution, the evaporation residue is dissolved in 2N sodium hydroxide solution and extracted with ether, and the aqueous phase is rendered acidic with 2N hydrochloric acid. The title compound is obtained by extracting with ethyl acetate, drying and evaporating as a colourless foam ($R_f$ 0.40, system A2), FAB-MS: m/e=514 (M+H)$^+$.

EXAMPLE 60

N-(2-Acetylamino-ethyl)-N-[(2'-(1H-tetrazol-5-yl)biphenyl-4-yl)methyl]-n-valeramide 9.9 g (22 mmol) of crude N-(2-acetylaminoethyl)-N-[2'-cyanobiphenyl-4-yl)methyl]-n-valeramide and 12.3 g (37 mmol) of tributyltin azide in 100 ml of xylene mixture are heated under reflux for 30 hours. The precipitate which deposits is isolated after cooling by decanting and then brought into solution by stirring between 100 ml of ether and 100 ml of 1N potassium hydroxide solution (3–4 hours). The title compound is isolated from the aqueous alkaline phase by acidifying with 2N HCl and extracting with a large quantity of ethyl acetate and purified by "flash" chromatography (system A2). The title compound is thus obtained as a solid having a melting interval of 74–80°.

The starting material can be prepared, for example, as follows:

a) N-[2-2'-Cyanobiphenyl-4-yl)methylamino)ethyl]acetamide

The title compound is obtained from 9.2 g (90 mmol) of 2-aminoethylacetamide and 8.1 g (30 mM) (sic) of 4-bromomethyl-2'-cyanobiphenyl in 100 ml of dioxane analogously to Example 23a as an oil which is further used in crude form.

b) N-[(2-Acetylaminoethyl)-N-[(2'-cyanobiphenyl-4-yl)methyl]-n-valeramide

A solution of 4.2 g (8.8 mmol) of the compound mentioned under a) and 5.0 ml of Hünig base in 40 ml of methylene chloride is treated with 2.4 g (20 mmol) of valeryl chloride and the mixture is heated to boiling under reflux for 24 hours. Working-up analogously to Example 23b and "flash"-chromatographic purification (n-hexane-ethyl acetate 4:1) give the title compound as a yellow oil of $R_f$ 0.17 (n-hexane-ethyl acetate 4:1).

EXAMPLE 61

N-Butyl N-[(2'-(1H-Tetrazol-5-yl)biphenyl-4-yl)methyl]-N-valeryl-1-aminomethylcyclopentane-1-carboxylate 0.490 g of N-[(2'-(1H-Tetrazol-5-yl)biphenyl-4-yl)methyl]-N-valeryl-1-aminomethylcyclopentane-1-carboxylic acid is dissolved in 20 ml of 1-butanol, treated with molecular sieve 4 Å and 0.5 ml of 4N hydrochloric acid and heated to reflux for 48 hours. The reaction mixture is evaporated in vacuo and purified on silica gel 60 (40–63 μm) using CH$_2$Cl$_2$—MeOH 95:5, $R_f$=0.73 (system N8). MS(FAB): $m/e$ 518 (M$^+$+H), 540 (M$^+$+Na).

EXAMPLE 62

Ethyl N-[(2'-(1H-tetrazol-5-yl)biphenyl-4-yl)methyl]-N-valeryl-1-aminomethylcyclohexane-1-carboxylate 8.70 g of ethyl N-[(2'-cyanobiphenyl-4-yl)methyl]-N-valeryl-1-aminomethylcyclohexane-1-carboxylate are reacted analogously to Example 1. The crude product is purified on silica gel 60 (40–63 μm) using CH$_2$Cl$_2$—MeOH 95:5, $R_f$=0.66 (system N8). MS (FAB): $m/e$ 504 (M$^+$+H), 526 (M$^+$+Na), 542 (M$^+$+K).

The starting material can be prepared, for example, as follows:

a) Ethyl 1-aminomethylcyclohexane-1-carboxylate is obtained by hydrogenating 72.08 g of ethyl 1-cyanocyclohexane-1-carboxylate (T. Kurihara et al. Tet. Lett. 1976, 2455) in the presence of 20 g of Raney nickel, at 45° C. and under normal pressure in 600 ml of ethanol which contains about 4% ammonia. After removing the catalyst and solvent, the product is obtained by distillation, boiling point 72–75° C. at 0.3 mbar.

b) Ethyl N-[(2'-cyanobiphenyl-4- yl)methyl]-1-aminomethylcyclohexane-1-carboxylate is obtained from 5.422 g of 4-bromomethyl-2'-cyanobiphenyl and 9.264 g of ethyl 1-aminomethyl-cyclohexane-1-carboxylate analogously to Example 41a) an d purified on silica gel 60 (40–63 μm) using CH$_2$Cl$_2$—MeOH 97.5:2.5, $R_f$=0.67 (system N6).

c) Ethyl N-[(2'-cyanobiphenyl-4-yl)methyl]-N-valeryl-1-aminomethyl-1-carboxyltate is obtained from 7.12 g of ethyl N-[(2'-cyanobiphenyl-4-yl)methyl]-1-aminomethylcyclohexane-1-carboxylate analogously to Example 1c) and is purified by extraction, $R_f$=0.68 (system N6).

EXAMPLE 63

N-[(2'-(1H-Tetrazol-5-yl)biphenyl-4-yl)methyl]-N-valeryl-1-aminomethylcyclopentane-1-carboxylic acid benzylamine 0.507 g of N-[(2'-(1H-tetrazol-5-yl)biphenyl-4-yl)methyl]-N-valeryl-1-aminomethylcyclopentane-1- carboxylic acid is reacted with 0.214 g of benzylamine analogously to Example 48 and the rude product is purified on silica gel 60 (40–63 μm) using CH$_2$Cl$_2$—MeOH 95:5, R$_f$=0.49 (system N8). MS (FAB): $^m$/$_e$ 551 (M$^+$+H), 573 (M$^+$+Na).

EXAMPLE 64

2-Ethyl-2-[N-[(2'-(1H-tetrazol-5-yl)biphenyl-4-yl) methyl]-N-valerylaminomethyl]-butyric acid 1.146 g of ethyl N-[(2'-(1H-tetrazol-5-yl)biphenyl-4-yl)methyl]-N-valeryl-2-aminomethyl-2-ethylbutyrate are dissolved in 10 ml of ethanol, treated with 4.66 ml of 2N NaOH solution and heated to reflux for 20 hours. After cooling to room temperature and addition of 4.66 ml of 2N hydrochloric acid, the mixture is evaporated. The product is isolated by chromatography on silica gel 60 (40–63 μm) using CH$_2$Cl$_2$—MeOH 80:20, R$_f$=0.38 (system N8). MS (FAB): $^m$/$_e$ 486 (M$^+$+Na), 502 (M$^+$+K).

EXAMPLE 65

Tablets, each containing 50 mg of the active ingredient, for example N-valeryl-N-[(2'-(1H-tetrazol-5-yl)biphenyl-4-yl)methyl]-(L)-alanine methyl ester, can be prepared as follows:

| Composition (10,000 tablets) | |
|---|---|
| Active ingredient | 500.0 g |
| Lactose | 500.0 g |
| Potato starch | 352.0 g |
| Gelatin | 8.0 g |
| Talc | 60.0 g |
| Magnesium stearate | 10.0 g |
| Silica (highly disperse) | 20.0 g |
| Ethanol | q.s |

The active ingredient is mixed with the lactose and 292 g of potato starch, and the mixture is moistened with an alcoholic solution of the gelatin and granulated by means of a sieve. After drying, the remainder of the potato starch, the talc, the magnesium stearate and the highly disperse silica are admixed and the mixture is compressed to give tablets of 145.0 mg weight and 50.0 mg active ingredient content each which, if desired, can be provided with breaking notches for finer adjustment of the dosage.

EXAMPLE 66

Film-coated tablets, each containing 100 mg of the active ingredient, for example N-valeryl-N-[(2'-(1H-tetrazol-5-yl) biphenyl-4-yl)methyl]-(L)-alanine methyl ester, . . . (sic) be prepared . . . (sic):

| Composition (10,000 tablets) | |
|---|---|
| Active ingredient | 100.00 g |
| Lactose | 100.00 g |
| Maize starch | 70.00 g |
| Talc | 8.50 g |
| Calcium stearate | 1.50 g |
| Hydroxypropylmethylcellulose | 2.36 g |
| Shellac | 0.64 g |
| Water | q.s. |
| Methylene chloride | q.s. |

The active ingredient, the lactose and 40 g of the maize starch are mixed and moistened and granulated using a paste prepared from 15 g of maize starch and water (with warming). The granules are dried, and the remainder of the maize starch, the talc and the calcium stearate are added and mixed with the granules. The mixture is compressed to give tablets (weight: 280 mg) and these are coated with a solution of the hydroxypropylmethylcellulose and the shellac in methylene chloride; final weight of the film-coated tablets: 283 mg.

EXAMPLE 67

Tablets or film-coated tablets, containing another compound according to the invention, for example as in one of Examples 1 to 64, can also be prepared in an analogous manner to that described in Examples 65 and 66.

What is claimed is:

1. A compound of the formula:

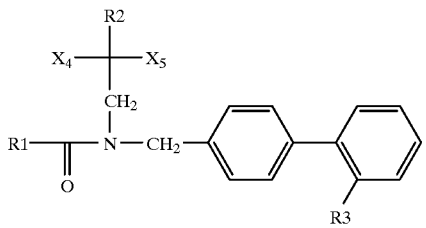

in which
R1 is alkyl of 1 to 7 carbon atoms;
R2 is hydroxy, carboxy, or alkoxycarbonyl in which alkoxy having from 1 to 7 carbon atoms;
R3 is carboxy or 1H-tetrazol-5-yl; and
X$_4$ and X$_5$ taken together are alkylene of 2 to 6 carbon atoms, or a pharmaceutically acceptable salt thereof.

2. The compound according to claim 1 in which
R1 is CH$_3$CH$_2$CH$_2$—, CH$_3$CH$_2$CH$_2$CH$_2$—, or CH$_3$CH$_2$CH$_2$CH$_2$CH$_2$—;
R2 is —COOH, —COOCH$_3$, or —COOCH$_2$CH$_3$; and
X$_4$ and X$_5$ taken together are —(CH$_2$)$_4$— or —(CH$_2$)$_5$—.

3. The compound according to claim 1 in which R1 is CH$_3$CH$_2$CH$_2$CH$_2$— and X$_4$ and X$_5$ taken together are —(CH$_2$)$_4$—.

4. The compound according to claim 1 in which R1 is CH$_3$CH$_2$CH$_2$CH$_2$— and X$_4$ and X$_5$ taken together are —(CH$_2$)$_5$—.

5. A pharmaceutical composition comprising a pharmaceutically acceptable carrier and a compound according to claim 1.

6. A method of treating hypertension in a warm blooded animal comprising administering to an animal in need of such treatment an effective amount of a compound according to claim 1.

* * * * *